(12) United States Patent
Prevost et al.

(10) Patent No.: US 11,291,554 B1
(45) Date of Patent: Apr. 5, 2022

(54) UNIBODY DUAL EXPANDING INTERBODY IMPLANT

(71) Applicant: Warsaw Orthopedic, Inc., Warsaw, IN (US)

(72) Inventors: Julien J. Prevost, Memphis, TN (US); Jonathan M. Dewey, Memphis, TN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

(21) Appl. No.: 17/246,968

(22) Filed: May 3, 2021

(51) Int. Cl.
*A61F 2/44* (2006.01)
*A61F 2/30* (2006.01)

(52) U.S. Cl.
CPC .......... *A61F 2/4425* (2013.01); *A61F 2/4455* (2013.01); *A61F 2002/30205* (2013.01); *A61F 2002/30433* (2013.01); *A61F 2002/443* (2013.01)

(58) Field of Classification Search
CPC ...... A61F 2/442; A61F 2/4455; A61F 2/4425; A61F 2002/443
USPC ............................................. 623/17.11–17.16
See application file for complete search history.

(56) References Cited

U.S. PATENT DOCUMENTS

| | | | |
|---|---|---|---|
| 4,401,112 A | 8/1983 | Rezaian | |
| 4,553,273 A | 11/1985 | Wu | |
| 4,636,217 A | 1/1987 | Ogilvie et al. | |
| 4,759,769 A | 7/1988 | Hedman et al. | |
| 5,059,193 A | 10/1991 | Kuslich | |
| 5,171,278 A | 12/1992 | Pisharodi | |
| 5,336,223 A | 8/1994 | Rogers | |
| 5,390,683 A | 2/1995 | Pisharodi | |
| 5,522,899 A | 6/1996 | Michelson | |

(Continued)

FOREIGN PATENT DOCUMENTS

| | | |
|---|---|---|
| DE | 44 16 605 C1 | 6/1995 |
| EP | 0 880 950 A1 | 12/1998 |

(Continued)

OTHER PUBLICATIONS

International Search Report, and Written Opinion for Application. No. PCT/US2019/019067, dated Jun. 3, 2019.

(Continued)

*Primary Examiner* — Eduardo C Robert
*Assistant Examiner* — Christina Negrellirodriguez
(74) *Attorney, Agent, or Firm* — Fox Rothschild LLP

(57) ABSTRACT

A unibody implant movable between an expanded position and a contracted position is disclosed. The implant may include a unitary expandable body defined by an inferior portion, a superior portion, and a medial portion that are connected together. The unibody implant may include a first set screw and a second set screw rotatably supported by the body. The first set screw may have a first inclined surface facing a proximal side and the second set screw may have a second inclined surface facing a distal side. The medial portion may include a first inclined ramp and the superior portion may include a second inclined ramp. Movement of the first set screw towards the proximal side urges the first inclined surface against the first inclined ramp and movement of the second set screw towards the distal side urges the second inclined surface against the second inclined ramp.

20 Claims, 30 Drawing Sheets

(56) References Cited

U.S. PATENT DOCUMENTS

| | | |
|---|---|---|
| 5,554,191 A | 9/1996 | Lahille et al. |
| 5,575,790 A | 11/1996 | Chen et al. |
| 5,609,635 A | 3/1997 | Michelson |
| 5,653,762 A | 8/1997 | Pisharodi |
| 5,658,336 A | 8/1997 | Pisharodi |
| 5,665,122 A | 9/1997 | Kambin |
| 5,693,100 A | 12/1997 | Pisharodi |
| 5,697,977 A | 12/1997 | Pisharodi |
| 5,702,391 A | 12/1997 | Lin |
| 5,702,453 A | 12/1997 | Rabbe et al. |
| 5,702,455 A | 12/1997 | Saggar |
| 5,797,918 A | 8/1998 | McGuire et al. |
| 5,800,550 A | 9/1998 | Sertich |
| 5,865,848 A | 2/1999 | Baker |
| 5,893,890 A | 4/1999 | Pisharodi |
| 5,931,777 A | 8/1999 | Sava |
| 5,980,522 A | 11/1999 | Koros et al. |
| 6,045,579 A | 4/2000 | Hochshuler et al. |
| 6,074,343 A | 6/2000 | Nathanson et al. |
| 6,080,193 A | 6/2000 | Hochshuler et al. |
| 6,099,531 A | 8/2000 | Bonutti |
| 6,102,949 A | 8/2000 | Biedermann et al. |
| 6,102,950 A | 8/2000 | Vaccaro |
| 6,106,557 A | 8/2000 | Robioneck et al. |
| 6,113,638 A | 9/2000 | Williams et al. |
| 6,117,174 A | 9/2000 | Nolan |
| 6,132,465 A | 10/2000 | Ray et al. |
| 6,159,211 A | 12/2000 | Boriani et al. |
| 6,159,244 A | 12/2000 | Suddaby |
| 6,176,882 B1 | 1/2001 | Biedermann et al. |
| 6,179,873 B1 | 1/2001 | Zientek |
| 6,190,414 B1 | 2/2001 | Young et al. |
| 6,193,757 B1 | 2/2001 | Foley et al. |
| 6,217,579 B1 | 4/2001 | Koros |
| 6,245,108 B1 | 6/2001 | Biscup |
| 6,309,421 B1 | 10/2001 | Pisharodi |
| 6,342,074 B1 | 1/2002 | Simpson |
| 6,371,989 B1 | 4/2002 | Chauvin et al. |
| 6,395,031 B1 | 5/2002 | Foley et al. |
| 6,423,063 B1 | 7/2002 | Bonutti |
| 6,432,106 B1 | 8/2002 | Fraser |
| 6,436,140 B1 | 8/2002 | Liu et al. |
| 6,443,989 B1 | 9/2002 | Jackson |
| 6,443,990 B1 | 9/2002 | Aebi et al. |
| 6,454,806 B1 | 9/2002 | Cohen et al. |
| 6,454,807 B1 | 9/2002 | Jackson |
| 6,461,359 B1 | 10/2002 | Tribus et al. |
| 6,491,724 B1 | 12/2002 | Ferree |
| 6,520,991 B2 | 2/2003 | Huene |
| 6,520,993 B2 | 2/2003 | James et al. |
| 6,527,803 B1 | 3/2003 | Crozet et al. |
| 6,562,074 B2 | 5/2003 | Gerbec et al. |
| 6,576,016 B1 | 6/2003 | Hochshuler et al. |
| 6,623,525 B2 | 9/2003 | Ralph et al. |
| 6,629,998 B1 | 10/2003 | Lin |
| 6,635,086 B2 | 10/2003 | Lin |
| 6,648,917 B2 | 11/2003 | Gerbec et al. |
| 6,676,703 B2 | 1/2004 | Biscup |
| 6,685,742 B1 | 2/2004 | Jackson |
| 6,723,126 B1 | 4/2004 | Berry |
| 6,770,096 B2 | 8/2004 | Bolger et al. |
| 6,773,460 B2 | 8/2004 | Jackson |
| 6,821,298 B1 | 11/2004 | Jackson |
| 6,835,206 B2 | 12/2004 | Jackson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,923,814 B2 | 8/2005 | Hildebrand et al. |
| 6,926,737 B2 | 8/2005 | Jackson |
| 6,953,477 B2 | 10/2005 | Berry |
| 6,964,687 B1 | 11/2005 | Bernard et al. |
| 6,974,480 B2 | 12/2005 | Messerli et al. |
| 6,984,234 B2 | 1/2006 | Bray |
| 7,112,222 B2 | 9/2006 | Fraser et al. |
| 7,135,043 B2 | 11/2006 | Nakahara et al. |
| 7,137,997 B2 | 11/2006 | Paul |
| 7,172,627 B2 | 2/2007 | Fiere et al. |
| 7,204,853 B2 | 4/2007 | Gordon et al. |
| 7,232,464 B2 | 6/2007 | Mathieu et al. |
| 7,238,203 B2 | 7/2007 | Bagga et al. |
| 7,316,714 B2 | 1/2008 | Gordon et al. |
| 7,407,483 B2 | 8/2008 | Perez-Cruet et al. |
| 7,481,766 B2 | 1/2009 | Lee et al. |
| 7,491,168 B2 | 2/2009 | Raymond et al. |
| 7,537,565 B2 | 5/2009 | Bass |
| 7,618,456 B2 | 11/2009 | Mathieu et al. |
| 7,625,394 B2 | 12/2009 | Molz, IV et al. |
| 7,655,046 B2 | 2/2010 | Dryer et al. |
| 7,678,148 B2 | 3/2010 | Peterman |
| 7,703,727 B2 | 4/2010 | Selness |
| 7,708,778 B2 | 5/2010 | Gordon et al. |
| 7,708,779 B2 | 5/2010 | Edie et al. |
| 7,727,280 B2 | 6/2010 | McLuen |
| 7,753,958 B2 | 7/2010 | Gordon et al. |
| 7,780,594 B2 | 8/2010 | Hutton |
| 7,806,932 B2 | 10/2010 | Webb et al. |
| 7,815,682 B1 | 10/2010 | Peterson et al. |
| 7,819,801 B2 | 10/2010 | Miles et al. |
| 7,828,849 B2 | 11/2010 | Lim |
| 7,846,167 B2 | 12/2010 | Garcia et al. |
| 7,846,207 B2 | 12/2010 | Lechmann et al. |
| 7,850,731 B2 | 12/2010 | Brittan et al. |
| 7,850,733 B2 | 12/2010 | Baynham et al. |
| 7,862,616 B2 | 1/2011 | Lechmann et al. |
| 7,875,076 B2 | 1/2011 | Mathieu et al. |
| 7,892,173 B2 | 2/2011 | Miles et al. |
| 7,909,869 B2 | 3/2011 | Gordon et al. |
| 7,914,559 B2 | 3/2011 | Carls et al. |
| 7,967,821 B2 | 6/2011 | Sicvol et al. |
| 7,981,031 B2 | 7/2011 | Frasier et al. |
| 8,016,836 B2 | 9/2011 | Corrao et al. |
| 8,062,375 B2 | 11/2011 | Glerum et al. |
| 8,105,382 B2 | 1/2012 | Olmos et al. |
| 8,118,870 B2 | 2/2012 | Gordon et al. |
| 8,118,871 B2 | 2/2012 | Gordon et al. |
| 8,123,810 B2 | 2/2012 | Gordon et al. |
| 8,147,550 B2 | 4/2012 | Gordon et al. |
| 8,172,903 B2 | 5/2012 | Gordon et al. |
| 8,182,539 B2 | 5/2012 | Tyber et al. |
| 8,257,442 B2 | 9/2012 | Edie et al. |
| 8,262,570 B2 | 9/2012 | White et al. |
| 8,262,662 B2 | 9/2012 | Beardsley et al. |
| 8,287,597 B1 | 10/2012 | Pimenta et al. |
| 8,303,498 B2 | 11/2012 | Miles et al. |
| 8,303,658 B2 | 11/2012 | Peterman |
| 8,303,663 B2 | 11/2012 | Jimenez et al. |
| 8,317,866 B2 | 11/2012 | Palmatier et al. |
| 8,323,185 B2 | 12/2012 | Perez-Cruet et al. |
| 8,328,872 B2 | 12/2012 | Duffield et al. |
| 8,343,048 B2 | 1/2013 | Warren, Jr. |
| 8,353,826 B2 | 1/2013 | Weiman |
| 8,355,780 B2 | 1/2013 | Miles et al. |
| 8,382,842 B2 | 2/2013 | Greenhalgh et al. |
| 8,388,527 B2 | 3/2013 | Miles et al. |
| 8,398,713 B2 | 3/2013 | Weiman |
| 8,403,990 B2 | 3/2013 | Dryer et al. |
| 8,419,797 B2 | 4/2013 | Biedermann et al. |
| 8,425,528 B2 | 4/2013 | Berry et al. |
| 8,435,298 B2 | 5/2013 | Weiman |
| 8,480,576 B2 | 7/2013 | Sandhu |
| 8,496,706 B2 | 7/2013 | Ragab et al. |
| 8,500,634 B2 | 8/2013 | Miles et al. |
| 8,506,635 B2 | 8/2013 | Palmatier et al. |
| 8,517,935 B2 | 8/2013 | Marchek et al. |
| 8,518,120 B2 | 8/2013 | Glerum et al. |
| 8,535,380 B2 | 9/2013 | Greenhalgh et al. |
| 8,550,994 B2 | 10/2013 | Miles et al. |
| 8,556,808 B2 | 10/2013 | Miles et al. |
| 8,556,979 B2 | 10/2013 | Glerum et al. |
| 8,579,809 B2 | 11/2013 | Parker |
| 8,579,979 B2 | 11/2013 | Edie et al. |
| 8,579,981 B2 | 11/2013 | Lim et al. |
| 8,602,984 B2 | 12/2013 | Raymond et al. |
| 8,628,576 B2 | 1/2014 | Triplett et al. |

(56) References Cited

U.S. PATENT DOCUMENTS

| | | |
|---|---|---|
| 8,628,578 B2 | 1/2014 | Miller et al. |
| 8,632,595 B2 | 1/2014 | Weiman |
| 8,641,768 B2 | 2/2014 | Duffield et al. |
| 8,647,386 B2 | 2/2014 | Gordon et al. |
| 8,663,329 B2 | 3/2014 | Ernst |
| 8,668,715 B2 | 3/2014 | Sandhu |
| 8,679,183 B2 | 3/2014 | Glerum et al. |
| 8,685,095 B2 | 4/2014 | Miller et al. |
| 8,685,098 B2 | 4/2014 | Glerum et al. |
| 8,696,559 B2 | 4/2014 | Miles et al. |
| 8,709,083 B2 | 4/2014 | Duffield et al. |
| 8,709,085 B2 | 4/2014 | Lechmann et al. |
| 8,709,086 B2 | 4/2014 | Glerum |
| 8,715,353 B2 | 5/2014 | Bagga et al. |
| 8,740,983 B1 | 6/2014 | Arnold et al. |
| 8,753,271 B1 | 6/2014 | Miles et al. |
| 8,753,396 B1 | 6/2014 | Hockett et al. |
| 8,764,649 B2 | 7/2014 | Miles et al. |
| 8,771,360 B2 | 7/2014 | Jimenez et al. |
| 8,778,025 B2 | 7/2014 | Ragab et al. |
| 8,778,027 B2 | 7/2014 | Medina |
| 8,795,366 B2 | 8/2014 | Varela |
| 8,808,305 B2 | 8/2014 | Kleiner |
| 8,827,902 B2 | 9/2014 | Dietze, Jr. et al. |
| 8,828,085 B1 | 9/2014 | Jensen |
| 8,840,668 B1 | 9/2014 | Donahoe et al. |
| 8,845,731 B2 | 9/2014 | Weiman |
| 8,845,732 B2 | 9/2014 | Weiman |
| 8,845,734 B2 | 9/2014 | Weiman |
| 8,852,282 B2 | 10/2014 | Farley et al. |
| 8,864,833 B2 | 10/2014 | Glerum et al. |
| 8,888,853 B2 | 11/2014 | Glerum et al. |
| 8,894,708 B2 | 11/2014 | Thalgott et al. |
| 8,894,711 B2 | 11/2014 | Varela |
| 8,894,712 B2 | 11/2014 | Varela |
| 8,906,095 B2 | 12/2014 | Christensen et al. |
| 8,920,500 B1 | 12/2014 | Pimenta et al. |
| 8,926,704 B2 | 1/2015 | Glerum et al. |
| 8,936,641 B2 | 1/2015 | Cain |
| 8,940,049 B1 | 1/2015 | Jimenez et al. |
| 8,968,363 B2 | 3/2015 | Weiman et al. |
| 8,986,344 B2 | 3/2015 | Sandhu |
| 8,992,425 B2 | 3/2015 | Karpowicz et al. |
| 8,992,544 B2 | 3/2015 | Sasing |
| 9,005,292 B2 | 4/2015 | Melamed |
| 9,005,293 B2 | 4/2015 | Moskowitz et al. |
| 9,005,295 B2 | 4/2015 | Kueenzi et al. |
| 9,017,412 B2 | 4/2015 | Wolters et al. |
| 9,034,045 B2 | 5/2015 | Davenport et al. |
| 9,050,146 B2 | 6/2015 | Woolley et al. |
| 9,050,194 B2 | 6/2015 | Thibodeau |
| 9,060,877 B2 | 6/2015 | Kleiner |
| 9,072,563 B2 | 7/2015 | Garcia et al. |
| 9,084,591 B2 | 7/2015 | Reglos et al. |
| 9,113,854 B2 | 8/2015 | Ellman |
| 9,119,730 B2 | 9/2015 | Glerum et al. |
| 9,125,757 B2 | 9/2015 | Weiman |
| 9,132,021 B2 | 9/2015 | Mermuys et al. |
| 9,138,217 B2 | 9/2015 | Smith et al. |
| 9,138,330 B2 | 9/2015 | Hansell et al. |
| 9,138,331 B2 | 9/2015 | Aferzon |
| 9,149,367 B2 | 10/2015 | Davenport et al. |
| 9,155,628 B2 | 10/2015 | Glerum et al. |
| 9,155,631 B2 | 10/2015 | Seifert et al. |
| 9,179,903 B2 | 11/2015 | Cianfrani et al. |
| 9,179,952 B2 | 11/2015 | Biedermann et al. |
| 9,186,193 B2 | 11/2015 | Kleiner et al. |
| 9,186,258 B2 | 11/2015 | Davenport et al. |
| 9,192,482 B1 | 11/2015 | Pimenta et al. |
| 9,192,483 B1 | 11/2015 | Radcliffe et al. |
| 9,198,772 B2 | 12/2015 | Weiman |
| 9,204,972 B2 | 12/2015 | Weiman et al. |
| 9,204,974 B2 | 12/2015 | Glerum et al. |
| 9,211,194 B2 | 12/2015 | Bagga et al. |
| 9,211,196 B2 | 12/2015 | Glerum et al. |
| 9,216,095 B2 | 12/2015 | Glerum et al. |
| 9,226,836 B2 | 1/2016 | Glerum |
| 9,233,007 B2 | 1/2016 | Sungarian et al. |
| 9,233,009 B2 | 1/2016 | Gray et al. |
| 9,233,010 B2 | 1/2016 | Thalgott et al. |
| 9,259,327 B2 | 2/2016 | Niemiec et al. |
| 9,271,846 B2 | 3/2016 | Lim et al. |
| 9,308,099 B2 | 4/2016 | Triplett et al. |
| 9,320,610 B2 | 4/2016 | Alheidt et al. |
| 9,351,845 B1 | 5/2016 | Pimenta et al. |
| 9,351,848 B2 | 5/2016 | Glerum et al. |
| 9,357,909 B2 | 6/2016 | Perez-Cruet et al. |
| 9,358,126 B2 | 6/2016 | Glerum et al. |
| 9,358,127 B2 | 6/2016 | Duffield et al. |
| 9,358,128 B2 | 6/2016 | Glerum et al. |
| 9,358,129 B2 | 6/2016 | Weiman |
| 9,364,343 B2 | 6/2016 | Duffield et al. |
| 9,370,434 B2 | 6/2016 | Weiman |
| 9,370,435 B2 | 6/2016 | Walkenhorst et al. |
| 9,381,008 B2 | 7/2016 | Thornburg |
| 9,386,916 B2 | 7/2016 | Predick et al. |
| 9,387,092 B2 | 7/2016 | Mermuys et al. |
| 9,402,673 B2 | 8/2016 | Cormier et al. |
| 9,402,739 B2 | 8/2016 | Weiman et al. |
| 9,408,596 B2 | 8/2016 | Blain |
| 9,408,708 B2 | 8/2016 | Greenhalgh |
| 9,414,828 B2 | 8/2016 | Abidin et al. |
| 9,414,934 B2 | 8/2016 | Cain |
| 9,414,937 B2 | 8/2016 | Carlson et al. |
| 9,421,110 B2 | 8/2016 | Masson et al. |
| 9,427,331 B2 | 8/2016 | Amin |
| 9,445,919 B2 | 9/2016 | Palmatier et al. |
| 9,452,063 B2 | 9/2016 | Glerum et al. |
| 9,456,903 B2 | 10/2016 | Glerum et al. |
| 9,456,906 B2 | 10/2016 | Gray et al. |
| 9,468,405 B2 | 10/2016 | Miles et al. |
| 9,474,622 B2 | 10/2016 | McLaughlin et al. |
| 9,474,625 B2 | 10/2016 | Weiman |
| 9,480,573 B2 | 11/2016 | Perloff et al. |
| 9,480,576 B2 | 11/2016 | Pepper et al. |
| 9,480,579 B2 | 11/2016 | Davenport et al. |
| 9,486,133 B2 | 11/2016 | Lee et al. |
| 9,486,325 B2 | 11/2016 | Davenport et al. |
| 9,486,327 B2 | 11/2016 | Martynova et al. |
| 9,486,328 B2 | 11/2016 | Jimenez et al. |
| 9,492,287 B2 | 11/2016 | Glerum et al. |
| 9,492,288 B2 | 11/2016 | Wagner et al. |
| 9,492,289 B2 | 11/2016 | Davenport et al. |
| 9,498,349 B2 | 11/2016 | Patterson et al. |
| 9,510,954 B2 | 12/2016 | Glerum et al. |
| 9,522,070 B2 | 12/2016 | Flower et al. |
| 9,526,620 B2 | 12/2016 | Slivka et al. |
| 9,526,625 B2 | 12/2016 | Cain |
| 9,532,821 B2 | 1/2017 | Moskowitz et al. |
| 9,539,103 B2 | 1/2017 | McLaughlin et al. |
| 9,539,108 B2 | 1/2017 | Glerum et al. |
| 9,545,320 B2 | 1/2017 | Padovani et al. |
| 9,549,723 B2 | 1/2017 | Hynes et al. |
| 9,549,824 B2 | 1/2017 | McAfee |
| 9,561,116 B2 | 2/2017 | Weiman et al. |
| 9,566,163 B2 | 2/2017 | Suddaby et al. |
| 9,566,166 B2 | 2/2017 | Parry et al. |
| 9,566,168 B2 | 2/2017 | Glerum et al. |
| 9,572,560 B2 | 2/2017 | Mast et al. |
| 9,572,677 B2 | 2/2017 | Davenport et al. |
| 9,572,681 B2 | 2/2017 | Mathieu et al. |
| 9,579,124 B2 | 2/2017 | Gordon et al. |
| 9,579,139 B2 | 2/2017 | Cormier et al. |
| 9,579,213 B2 | 2/2017 | Bal et al. |
| 9,585,649 B2 | 3/2017 | Blain et al. |
| 9,585,762 B2 | 3/2017 | Suddaby et al. |
| 9,585,766 B2 | 3/2017 | Robinson |
| 9,585,767 B2 | 3/2017 | Robinson |
| 9,592,129 B2 | 3/2017 | Slivka et al. |
| 9,597,195 B2 | 3/2017 | Cain |
| 9,603,713 B2 | 3/2017 | Moskowitz et al. |
| 9,603,717 B2 | 3/2017 | Ibarra et al. |
| 9,615,818 B2 | 4/2017 | Baudouin et al. |
| 9,615,936 B2 | 4/2017 | Duffield et al. |

(56) References Cited

U.S. PATENT DOCUMENTS

| | | |
|---|---|---|
| 9,622,732 B2 | 4/2017 | Martinelli et al. |
| 9,622,875 B2 | 4/2017 | Moskowitz et al. |
| 9,622,876 B1 | 4/2017 | Greenhalgh et al. |
| 9,629,729 B2 | 4/2017 | Grimberg, Jr. et al. |
| 9,636,097 B2 | 5/2017 | Bass |
| 9,642,720 B2 | 5/2017 | Radcliffe et al. |
| 9,649,198 B2 | 5/2017 | Wolters et al. |
| 9,655,746 B2 | 5/2017 | Seifert |
| 9,655,747 B2 | 5/2017 | Glerum et al. |
| 9,662,224 B2 | 5/2017 | Weiman et al. |
| 9,668,784 B2 | 6/2017 | Brumfield et al. |
| 9,668,876 B2 | 6/2017 | Blain et al. |
| 9,668,879 B2 | 6/2017 | Jimenez et al. |
| 9,675,465 B2 | 6/2017 | Padovani et al. |
| 9,675,467 B2 | 6/2017 | Duffield et al. |
| 9,675,468 B1 | 6/2017 | Jensen |
| 9,693,871 B2 | 7/2017 | Richerme et al. |
| 9,700,428 B2 | 7/2017 | Niemiec et al. |
| 9,707,092 B2 | 7/2017 | Davenport et al. |
| 9,713,536 B2 | 7/2017 | Foley et al. |
| 9,717,601 B2 | 8/2017 | Miller |
| 9,730,684 B2 | 8/2017 | Beale et al. |
| 9,730,806 B2 | 8/2017 | Capote |
| 9,737,288 B2 | 8/2017 | Karpowicz et al. |
| 9,750,617 B2 | 9/2017 | Lim et al. |
| 9,750,618 B1 | 9/2017 | Daffinson et al. |
| 9,757,249 B2 | 9/2017 | Radcliffe et al. |
| 9,770,343 B2 | 9/2017 | Weiman |
| 9,782,265 B2 | 10/2017 | Weiman et al. |
| 9,788,971 B1 | 10/2017 | Stein |
| 9,795,370 B2 | 10/2017 | O'Connell et al. |
| 9,795,371 B2 | 10/2017 | Miles et al. |
| 9,801,733 B2 | 10/2017 | Wolters et al. |
| 9,801,734 B1 | 10/2017 | Stein et al. |
| 9,808,352 B2 | 11/2017 | Suddaby et al. |
| 9,826,966 B2 | 11/2017 | Mast et al. |
| 9,827,024 B2 | 11/2017 | Cormier et al. |
| 9,827,107 B1 | 11/2017 | Amin |
| 9,833,333 B2 | 12/2017 | Duffield et al. |
| 9,833,336 B2 | 12/2017 | Davenport et al. |
| 9,839,527 B2 | 12/2017 | Robinson |
| 9,839,528 B2 | 12/2017 | Weiman et al. |
| 9,848,993 B2 | 12/2017 | Moskowitz et al. |
| 9,848,996 B2 | 12/2017 | Faulhaber |
| 9,855,151 B2 | 1/2018 | Weiman |
| 9,867,715 B2 | 1/2018 | McLaughlin et al. |
| 9,872,779 B2 | 1/2018 | Miller et al. |
| 9,889,019 B2 | 2/2018 | Rogers et al. |
| 9,907,671 B2 | 3/2018 | Fessler |
| 9,907,673 B2 | 3/2018 | Weiman et al. |
| 9,918,709 B2 | 3/2018 | Sandhu |
| 9,924,859 B2 | 3/2018 | Lee et al. |
| 9,924,940 B2 | 3/2018 | Moskowitz et al. |
| 9,925,062 B2 | 3/2018 | Glerum et al. |
| 9,925,064 B2 | 3/2018 | Duffield et al. |
| 9,931,223 B2 | 4/2018 | Cain |
| 9,937,053 B2 | 4/2018 | Melkent et al. |
| 9,943,342 B2 | 4/2018 | Tanaka et al. |
| 9,943,418 B2 | 4/2018 | Davenport et al. |
| 9,949,841 B2 | 4/2018 | Glerum et al. |
| 9,956,087 B2 | 5/2018 | Seifert et al. |
| 9,962,270 B2 * | 5/2018 | Alheidt ................. A61F 2/4611 |
| 9,962,271 B2 | 5/2018 | Glerum |
| 9,962,272 B1 | 5/2018 | Daffinson et al. |
| 9,968,461 B2 | 5/2018 | Zappacosta et al. |
| 9,968,462 B2 | 5/2018 | Weiman |
| 9,974,531 B2 | 5/2018 | Miles et al. |
| 9,974,662 B2 | 5/2018 | Hessler et al. |
| 9,974,664 B2 | 5/2018 | Emerick et al. |
| 9,980,825 B2 | 5/2018 | Nichols et al. |
| 9,980,826 B2 | 5/2018 | Martynova et al. |
| 9,987,141 B2 | 6/2018 | Duffield et al. |
| 9,987,143 B2 | 6/2018 | Robinson et al. |
| 9,987,144 B2 | 6/2018 | Seifert et al. |
| 9,987,146 B1 | 6/2018 | Lentner et al. |
| 9,993,239 B2 | 6/2018 | Karpowicz et al. |
| 9,993,350 B2 | 6/2018 | Cain |
| 10,004,607 B2 | 6/2018 | Weiman et al. |
| 10,016,282 B2 | 7/2018 | Seifert et al. |
| 10,016,284 B2 | 7/2018 | Moskowitz et al. |
| 10,022,239 B1 | 7/2018 | Lentner et al. |
| 10,028,842 B2 | 7/2018 | Gray et al. |
| 10,034,765 B2 | 7/2018 | Blain et al. |
| 10,034,769 B2 | 7/2018 | Baynham |
| 10,034,772 B2 | 7/2018 | Glerum et al. |
| 10,034,773 B2 | 7/2018 | McLaughlin et al. |
| 10,039,539 B2 | 8/2018 | Friedrich et al. |
| 10,039,650 B2 | 8/2018 | Lamborne et al. |
| 10,052,214 B2 | 8/2018 | Jimenez et al. |
| 10,060,469 B2 | 8/2018 | Jimenez et al. |
| 10,070,852 B2 | 9/2018 | Mast et al. |
| 10,076,320 B2 | 9/2018 | Mast et al. |
| 10,076,423 B2 | 9/2018 | Miller et al. |
| 10,080,666 B2 | 9/2018 | Suddaby et al. |
| 10,080,669 B2 | 9/2018 | Davenport et al. |
| 10,085,846 B2 | 10/2018 | Grotz |
| 10,085,849 B2 | 10/2018 | Weiman et al. |
| 10,092,417 B2 | 10/2018 | Weiman et al. |
| 10,098,758 B2 | 10/2018 | Matthews et al. |
| 10,098,759 B2 | 10/2018 | Weiman |
| 10,111,755 B2 | 10/2018 | Foley et al. |
| 10,111,758 B2 | 10/2018 | Robinson |
| 10,117,754 B2 | 11/2018 | Davenport et al. |
| 10,117,755 B2 | 11/2018 | Emerick et al. |
| 10,137,002 B2 | 11/2018 | Padovani et al. |
| 10,137,006 B2 | 11/2018 | Dewey et al. |
| 10,137,007 B2 | 11/2018 | Dewey et al. |
| 10,137,009 B2 | 11/2018 | Weiman et al. |
| 10,149,671 B2 | 12/2018 | Predick et al. |
| 10,149,710 B2 | 12/2018 | Tanaka et al. |
| 10,154,781 B2 | 12/2018 | Weiman |
| 10,154,912 B2 | 12/2018 | Glerum |
| 10,154,914 B2 | 12/2018 | Robinson |
| 10,159,584 B2 | 12/2018 | Carnes et al. |
| 10,166,117 B1 | 1/2019 | Daffinson et al. |
| 10,172,515 B2 | 1/2019 | Lee et al. |
| 10,172,652 B2 | 1/2019 | Woolley et al. |
| 10,178,987 B2 | 1/2019 | Predick et al. |
| 10,179,053 B2 | 1/2019 | Zappacosta et al. |
| 10,182,922 B2 | 1/2019 | Nichols et al. |
| 10,188,527 B2 | 1/2019 | Rogers et al. |
| 10,195,050 B2 | 2/2019 | Palmatier et al. |
| 10,201,431 B2 | 2/2019 | Slater et al. |
| 10,213,192 B2 | 2/2019 | Capote |
| 10,213,193 B2 | 2/2019 | Karpowicz et al. |
| 10,219,798 B2 | 3/2019 | Capote |
| 10,219,913 B2 | 3/2019 | Matthews et al. |
| 10,219,914 B2 | 3/2019 | Faulhaber |
| 10,219,915 B1 | 3/2019 | Stein |
| 10,226,356 B2 | 3/2019 | Grotz |
| 10,226,359 B2 | 3/2019 | Glerum et al. |
| 10,238,375 B2 | 3/2019 | O'Connell et al. |
| 10,238,383 B2 | 3/2019 | Moskowitz et al. |
| 10,238,503 B2 | 3/2019 | Branch et al. |
| 10,245,015 B2 | 4/2019 | Predick et al. |
| 10,251,643 B2 | 4/2019 | Moskowitz et al. |
| 10,265,191 B2 | 4/2019 | Lim et al. |
| 10,278,686 B2 | 5/2019 | Baudouin et al. |
| 10,278,786 B2 | 5/2019 | Friedrich et al. |
| 10,278,830 B1 | 5/2019 | Walker et al. |
| 10,278,831 B2 | 5/2019 | Sandul |
| 10,278,832 B2 | 5/2019 | Nichols et al. |
| 10,285,680 B2 | 5/2019 | Friedrich et al. |
| 10,285,819 B2 | 5/2019 | Greenhalgh |
| 10,285,824 B2 | 5/2019 | Robinson |
| 10,292,828 B2 | 5/2019 | Greenhalgh |
| 10,299,777 B2 | 5/2019 | Mast et al. |
| 10,299,934 B2 | 5/2019 | Seifert et al. |
| 10,299,937 B2 | 5/2019 | McAfee |
| 10,307,268 B2 | 6/2019 | Moskowitz et al. |
| 10,314,719 B2 | 6/2019 | Hessler et al. |
| 10,322,007 B2 | 6/2019 | Masson et al. |
| 10,322,009 B2 | 6/2019 | Aghayev et al. |
| 10,327,909 B2 | 6/2019 | Baynham |

(56) References Cited

U.S. PATENT DOCUMENTS

| | | |
|---|---|---|
| 10,327,912 B1 | 6/2019 | Suddaby |
| 10,327,917 B2 | 6/2019 | Glerum et al. |
| 10,342,675 B2 | 7/2019 | Alheidt |
| 10,350,085 B2 | 7/2019 | Glerum et al. |
| 10,357,233 B2 | 7/2019 | Miles et al. |
| 10,363,142 B2 | 7/2019 | McClintock et al. |
| 10,363,144 B2 | 7/2019 | Overes et al. |
| 10,369,004 B2 | 8/2019 | Faulhaber |
| 10,369,008 B2 | 8/2019 | Jimenez et al. |
| 10,369,010 B2 | 8/2019 | Robinson et al. |
| 10,369,012 B2 | 8/2019 | Fessler |
| 10,376,377 B2 | 8/2019 | Seifert et al. |
| 10,390,962 B2 | 8/2019 | Weiman |
| 10,390,964 B2 | 8/2019 | Faulhaber |
| 10,398,563 B2 | 9/2019 | Engstrom |
| 10,398,566 B2 | 9/2019 | Olmos et al. |
| 10,413,419 B2 | 9/2019 | Thibodeau |
| 10,413,422 B2 | 9/2019 | Flower et al. |
| 10,413,423 B2 | 9/2019 | Overes et al. |
| 10,426,450 B2 | 10/2019 | Vogel et al. |
| 10,426,633 B2 | 10/2019 | Moskowitz et al. |
| 10,426,634 B1 | 10/2019 | Al-Jazaeri et al. |
| 10,441,430 B2 | 10/2019 | Ludwig et al. |
| 10,449,056 B2 | 10/2019 | Cain |
| 10,456,122 B2 | 10/2019 | Koltz et al. |
| 10,470,894 B2 | 11/2019 | Foley et al. |
| 10,478,319 B2 | 11/2019 | Moskowitz et al. |
| 10,492,912 B2 | 12/2019 | Gregersen et al. |
| 10,492,922 B2 | 12/2019 | Mathieu et al. |
| 10,492,924 B2 | 12/2019 | Stein et al. |
| 10,500,064 B2 | 12/2019 | Robinson |
| 10,512,550 B2 | 12/2019 | Bechtel et al. |
| 10,517,645 B2 | 12/2019 | van der Pol |
| 10,524,924 B2 | 1/2020 | Davenport et al. |
| 10,531,903 B2 | 1/2020 | Daly et al. |
| 10,537,436 B2 | 1/2020 | Maguire et al. |
| 10,537,438 B2 | 1/2020 | Martynova et al. |
| 10,555,729 B1 | 2/2020 | Cole et al. |
| 10,561,411 B1 | 2/2020 | Cole et al. |
| 10,575,960 B2 | 3/2020 | Duffield et al. |
| 10,583,015 B2 | 3/2020 | Olmos et al. |
| 10,603,078 B2 | 3/2020 | Simpson et al. |
| 10,610,376 B2 | 4/2020 | Kuyler et al. |
| 10,624,757 B2 | 4/2020 | Bost et al. |
| 10,624,758 B2 | 4/2020 | Slivka et al. |
| 10,624,761 B2 | 4/2020 | Davenport et al. |
| 10,639,166 B2 | 5/2020 | Weiman et al. |
| 10,667,925 B2 | 6/2020 | Emerick et al. |
| 10,667,927 B2 | 6/2020 | Lamborne et al. |
| 10,675,157 B2 | 6/2020 | Zakelj et al. |
| 10,682,241 B2 | 6/2020 | Glerum et al. |
| 10,687,963 B2 | 6/2020 | Jimenez et al. |
| 10,702,393 B2 | 7/2020 | Davenport et al. |
| 10,709,569 B2 | 7/2020 | McLaughlin et al. |
| 10,709,571 B2 | 7/2020 | Iott et al. |
| 10,709,572 B2 | 7/2020 | Daffinson et al. |
| 10,709,575 B2 | 7/2020 | Robinson |
| 10,722,377 B2 | 7/2020 | Glerum et al. |
| 10,722,379 B2 | 7/2020 | McLaughlin et al. |
| 10,729,561 B2 | 8/2020 | Glerum |
| 10,743,858 B1 | 8/2020 | Cole et al. |
| 10,744,002 B2 | 8/2020 | Glerum et al. |
| 10,758,366 B2 | 9/2020 | Daffinson et al. |
| 10,758,367 B2 | 9/2020 | Weiman et al. |
| 10,758,369 B2 | 9/2020 | Rogers et al. |
| 10,765,528 B2 | 9/2020 | Weiman et al. |
| 10,772,737 B2 | 9/2020 | Gray et al. |
| 10,779,955 B2 | 9/2020 | Kuyler et al. |
| 10,779,957 B2 | 9/2020 | Weiman et al. |
| 10,786,364 B2 | 9/2020 | Davenport et al. |
| 10,786,369 B2 | 9/2020 | Carnes et al. |
| 10,799,368 B2 | 10/2020 | Glerum et al. |
| 10,835,387 B2 | 11/2020 | Weiman et al. |
| 10,842,640 B2 | 11/2020 | Weiman et al. |
| 10,842,644 B2 | 11/2020 | Weiman et al. |
| 10,856,997 B2 | 12/2020 | Cowan et al. |
| 10,869,769 B2 | 12/2020 | Eisen et al. |
| 10,874,523 B2 | 12/2020 | Weiman et al. |
| 10,874,524 B2 | 12/2020 | Bjork |
| 2002/0045943 A1 | 4/2002 | Uk |
| 2002/0045945 A1 | 4/2002 | Liu et al. |
| 2002/0116066 A1 | 8/2002 | Chauvin et al. |
| 2002/0128713 A1 | 9/2002 | Ferree |
| 2002/0151976 A1 | 10/2002 | Foley et al. |
| 2003/0050701 A1 | 3/2003 | Michelson |
| 2003/0130739 A1 | 7/2003 | Gerbec et al. |
| 2004/0172134 A1 | 9/2004 | Berry |
| 2004/0186570 A1 | 9/2004 | Rapp |
| 2004/0193158 A1 | 9/2004 | Lim et al. |
| 2004/0249461 A1 | 12/2004 | Ferree |
| 2004/0254643 A1 | 12/2004 | Jackson |
| 2004/0254644 A1 | 12/2004 | Taylor |
| 2005/0015149 A1 | 1/2005 | Michelson |
| 2005/0033429 A1 | 2/2005 | Kuo |
| 2005/0033439 A1 | 2/2005 | Gordon et al. |
| 2006/0122701 A1 | 6/2006 | Kiester |
| 2006/0129244 A1 | 6/2006 | Ensign |
| 2009/0024158 A1 | 1/2009 | Viker |
| 2009/0292361 A1 | 11/2009 | Lopez |
| 2010/0082109 A1 | 4/2010 | Greenhalgh et al. |
| 2010/0191336 A1 | 7/2010 | Greenhalgh |
| 2010/0211176 A1 | 8/2010 | Greenhalgh |
| 2011/0118843 A1 | 5/2011 | Mathieu et al. |
| 2011/0130838 A1 | 6/2011 | Morgenstern Lopez |
| 2011/0218572 A1 | 9/2011 | Lechmann et al. |
| 2012/0101581 A1 | 4/2012 | Mathieu et al. |
| 2012/0109142 A1 | 5/2012 | Dayan |
| 2012/0109309 A1 | 5/2012 | Mathieu et al. |
| 2012/0109310 A1 | 5/2012 | Mathieu et al. |
| 2012/0109312 A1 | 5/2012 | Mathieu et al. |
| 2012/0109313 A1 | 5/2012 | Mathieu et al. |
| 2012/0123546 A1 | 5/2012 | Medina |
| 2012/0197401 A1 | 8/2012 | Duncan et al. |
| 2012/0209385 A1 | 8/2012 | Aferzon |
| 2012/0215316 A1 | 8/2012 | Mohr et al. |
| 2013/0190876 A1 | 7/2013 | Drochner et al. |
| 2013/0226191 A1 | 8/2013 | Thoren et al. |
| 2013/0231747 A1 | 9/2013 | Olmos et al. |
| 2013/0317312 A1 | 11/2013 | Eastlack et al. |
| 2014/0107790 A1 | 4/2014 | Combrowski |
| 2014/0114420 A1 | 4/2014 | Robinson |
| 2014/0163682 A1 | 6/2014 | Iott et al. |
| 2014/0180419 A1 | 6/2014 | Dmuschewsky |
| 2014/0194992 A1 | 7/2014 | Medina |
| 2014/0277500 A1 | 9/2014 | Logan et al. |
| 2015/0223945 A1 | 8/2015 | Weiman et al. |
| 2015/0230931 A1 | 8/2015 | Greenhalgh |
| 2016/0008924 A1 | 1/2016 | Canourgues et al. |
| 2016/0022434 A1 | 1/2016 | Robinson |
| 2016/0081681 A1 | 3/2016 | Waugh et al. |
| 2016/0089247 A1 | 3/2016 | Nichols et al. |
| 2016/0095710 A1 | 4/2016 | Juszczyk et al. |
| 2016/0242930 A1 | 8/2016 | Duffield et al. |
| 2016/0256291 A1 | 9/2016 | Miller |
| 2016/0296340 A1 | 10/2016 | Gordon et al. |
| 2016/0310291 A1 | 10/2016 | Greenhalgh |
| 2016/0345952 A1 | 12/2016 | Kucharzyk et al. |
| 2016/0367377 A1 | 12/2016 | Faulhaber |
| 2017/0010025 A1 | 1/2017 | Mayershofer |
| 2017/0029635 A1 | 2/2017 | Doll et al. |
| 2017/0035406 A1 | 2/2017 | Abidin et al. |
| 2017/0049651 A1 | 2/2017 | Lim et al. |
| 2017/0049653 A1 | 2/2017 | Lim et al. |
| 2017/0095345 A1 | 4/2017 | Davenport et al. |
| 2017/0100255 A1 | 4/2017 | Hleihil et al. |
| 2017/0100257 A1 | 4/2017 | Weiman et al. |
| 2017/0105844 A1 | 4/2017 | Kuyler et al. |
| 2017/0151065 A1 | 6/2017 | Warren et al. |
| 2017/0156882 A1 | 6/2017 | Rathbun et al. |
| 2017/0156884 A1 | 6/2017 | Rathbun et al. |
| 2017/0189204 A1 | 7/2017 | Riemhofer et al. |
| 2017/0202678 A1 | 7/2017 | Duffield et al. |
| 2017/0215856 A1 | 8/2017 | Martinelli et al. |
| 2017/0224502 A1 | 8/2017 | Wolters et al. |

(56) References Cited

U.S. PATENT DOCUMENTS

| | | |
|---|---|---|
| 2017/0246006 A1 | 8/2017 | Carnes et al. |
| 2017/0290677 A1 | 10/2017 | Olmos et al. |
| 2017/0296352 A1 | 10/2017 | Richerme et al. |
| 2017/0367842 A1 | 12/2017 | Predick et al. |
| 2017/0367843 A1 | 12/2017 | Eisen et al. |
| 2017/0367844 A1 | 12/2017 | Eisen et al. |
| 2017/0367845 A1 | 12/2017 | Eisen et al. |
| 2018/0030362 A1 | 2/2018 | Kosler et al. |
| 2018/0031810 A1 | 2/2018 | Hsu et al. |
| 2018/0036136 A1 | 2/2018 | Duffield et al. |
| 2018/0036138 A1 | 2/2018 | Robinson |
| 2018/0116891 A1 | 5/2018 | Beale et al. |
| 2018/0193164 A1 | 7/2018 | Shoshtaev |
| 2018/0206999 A1 | 7/2018 | Suddaby |
| 2018/0256356 A1 | 9/2018 | Robinson et al. |
| 2018/0256359 A1 | 9/2018 | Greenhalgh |
| 2018/0256360 A1 | 9/2018 | Cain |
| 2018/0256362 A1 | 9/2018 | Slivka et al. |
| 2018/0263784 A1 | 9/2018 | Bechtel et al. |
| 2018/0280142 A1 | 10/2018 | Schultz et al. |
| 2018/0303473 A1 | 10/2018 | Spann et al. |
| 2018/0303621 A1 | 10/2018 | Brotman et al. |
| 2018/0303625 A1 | 10/2018 | Alheidt et al. |
| 2018/0311048 A1 | 11/2018 | Glerum et al. |
| 2018/0318101 A1 | 11/2018 | Engstrom |
| 2018/0318102 A1 | 11/2018 | Seifert et al. |
| 2018/0338838 A1 | 11/2018 | Cryder et al. |
| 2018/0338841 A1 | 11/2018 | Miller et al. |
| 2018/0344307 A1 | 12/2018 | Hynes et al. |
| 2018/0360616 A1 | 12/2018 | Luu |
| 2019/0000640 A1 | 1/2019 | Weiman |
| 2019/0000702 A1 | 1/2019 | Lim et al. |
| 2019/0000707 A1 | 1/2019 | Lim et al. |
| 2019/0020121 A1 | 1/2019 | Paulotto et al. |
| 2019/0021716 A1 | 1/2019 | Waugh et al. |
| 2019/0021873 A1 | 1/2019 | Dmuschewsky |
| 2019/0046329 A1 | 2/2019 | Padovani et al. |
| 2019/0046381 A1 | 2/2019 | Lim et al. |
| 2019/0046383 A1 | 2/2019 | Lim et al. |
| 2019/0060083 A1 | 2/2019 | Weiman et al. |
| 2019/0082949 A1 | 3/2019 | Weiman |
| 2019/0083081 A1 | 3/2019 | Ortiz et al. |
| 2019/0091033 A1 | 3/2019 | Dewey et al. |
| 2019/0105175 A1 | 4/2019 | Zappacosta et al. |
| 2019/0125328 A1 | 5/2019 | Blain |
| 2019/0133434 A1 | 5/2019 | Lee et al. |
| 2019/0133645 A1 | 5/2019 | Gordon et al. |
| 2019/0133780 A1 | 5/2019 | Matthews et al. |
| 2019/0133784 A1 | 5/2019 | Gunn et al. |
| 2019/0133788 A1 | 5/2019 | Weiman et al. |
| 2019/0142480 A1 | 5/2019 | Woolley et al. |
| 2019/0151115 A1 | 5/2019 | Nichols et al. |
| 2019/0183656 A1 | 6/2019 | Stein |
| 2019/0201209 A1 | 7/2019 | Branch et al. |
| 2019/0201210 A1 | 7/2019 | Besaw et al. |
| 2019/0209155 A1 | 7/2019 | Mast et al. |
| 2019/0216453 A1 | 7/2019 | Predick et al. |
| 2019/0231552 A1 | 8/2019 | Sandul |
| 2019/0240039 A1 | 8/2019 | Walker et al. |
| 2019/0240043 A1 | 8/2019 | Greenhalgh |
| 2019/0254650 A1 | 8/2019 | Martinelli et al. |
| 2019/0254838 A1 | 8/2019 | Miller et al. |
| 2019/0254839 A1 | 8/2019 | Nichols et al. |
| 2019/0262139 A1 | 8/2019 | Wolters |
| 2019/0269521 A1 | 9/2019 | Shoshtaev |
| 2019/0274670 A1 | 9/2019 | O'Connell et al. |
| 2019/0274671 A1 | 9/2019 | Lauf et al. |
| 2019/0274836 A1 | 9/2019 | Eisen et al. |
| 2019/0282373 A1 | 9/2019 | Alheidt |
| 2019/0290446 A1 | 9/2019 | Masson et al. |
| 2019/0290447 A1 | 9/2019 | Stein |
| 2019/0298416 A1 | 10/2019 | Rezach |
| 2019/0298524 A1 | 10/2019 | Lauf et al. |
| 2019/0298540 A1 | 10/2019 | Aghayev et al. |
| 2019/0321022 A1 | 10/2019 | Karpowicz et al. |
| 2019/0321190 A1 | 10/2019 | Wagner et al. |
| 2019/0328540 A1 | 10/2019 | Seifert et al. |
| 2019/0336301 A1 | 11/2019 | Engstrom |
| 2019/0336304 A1 | 11/2019 | Burkhardt et al. |
| 2019/0350573 A1 | 11/2019 | Vogel et al. |
| 2019/0358049 A1 | 11/2019 | Faulhaber |
| 2019/0358050 A1 | 11/2019 | Fessler |
| 2019/0358051 A1 | 11/2019 | Flower et al. |
| 2019/0380840 A1 | 12/2019 | Tyber et al. |
| 2019/0388232 A1 | 12/2019 | Purcell et al. |
| 2020/0008951 A1 | 1/2020 | McClintock et al. |
| 2020/0030114 A1 | 1/2020 | Cain |
| 2020/0030116 A1 | 1/2020 | Jimenez et al. |
| 2020/0038200 A1 | 2/2020 | Foley et al. |
| 2020/0054461 A1 | 2/2020 | Marrocco et al. |
| 2020/0060844 A1 | 2/2020 | Mathieu et al. |
| 2020/0078190 A1 | 3/2020 | Rogers et al. |
| 2020/0093607 A1 | 3/2020 | Davenport et al. |
| 2020/0093609 A1 | 3/2020 | Shoshtaev |
| 2020/0100904 A1 | 4/2020 | Stein et al. |
| 2020/0129306 A1 | 4/2020 | Miller et al. |
| 2020/0129307 A1 | 4/2020 | Hunziker et al. |
| 2020/0138591 A1 | 5/2020 | Moskowitz et al. |
| 2020/0138593 A1 | 5/2020 | Martynova et al. |
| 2020/0146840 A1 | 5/2020 | Black et al. |
| 2020/0205993 A1 | 7/2020 | Davenport et al. |
| 2020/0222202 A1 | 7/2020 | Kuyler et al. |
| 2020/0229944 A1 | 7/2020 | Suh et al. |
| 2020/0246159 A1 | 8/2020 | Suh et al. |
| 2020/0246162 A1 | 8/2020 | Schultz et al. |
| 2020/0261242 A1 | 8/2020 | Bost et al. |
| 2020/0268524 A1 | 8/2020 | Glerum et al. |
| 2020/0276028 A1 | 9/2020 | Blain et al. |
| 2020/0289287 A1 | 9/2020 | Emerick et al. |
| 2020/0297507 A1 | 9/2020 | Iott et al. |
| 2020/0330239 A1 | 10/2020 | Davenport et al. |
| 2020/0330245 A1 | 10/2020 | Glerum |
| 2020/0345511 A1 | 11/2020 | Daffinson et al. |
| 2020/0352731 A1 | 11/2020 | Berry |
| 2020/0352738 A1 | 11/2020 | Berry |
| 2020/0360153 A1 | 11/2020 | Weiman et al. |
| 2020/0375753 A1 | 12/2020 | McLaughlin et al. |
| 2020/0375755 A1 | 12/2020 | Cain |
| 2020/0383797 A1 | 12/2020 | Predick et al. |
| 2020/0383799 A1 | 12/2020 | Cain |
| 2020/0390565 A1 | 12/2020 | Jimenez et al. |
| 2020/0397593 A1 | 12/2020 | Davenport et al. |
| 2020/0405498 A1 | 12/2020 | Gray et al. |
| 2020/0405499 A1 | 12/2020 | Gerbec et al. |
| 2020/0405500 A1 | 12/2020 | Cain |

FOREIGN PATENT DOCUMENTS

| | | |
|---|---|---|
| EP | 0 767 636 B1 | 1/1999 |
| EP | 0 857 042 B1 | 11/2001 |
| EP | 1 442 732 A1 | 8/2004 |
| EP | 1 124 512 B1 | 9/2004 |
| EP | 1 107 711 B1 | 10/2004 |
| EP | 1 506 753 A1 | 2/2005 |
| EP | 1 459 711 B1 | 7/2007 |
| FR | 3082115 A1 | 12/2019 |
| GB | 2 377 387 A | 1/2003 |
| WO | 92/14423 A1 | 9/1992 |
| WO | 97/ 00054 A1 | 1/1997 |
| WO | 99/ 26562 A1 | 6/1999 |
| WO | 99/66867 A1 | 12/1999 |
| WO | 00/12033 A1 | 3/2000 |
| WO | 00/25706 A1 | 5/2000 |
| WO | 00/ 49977 A1 | 8/2000 |
| WO | 02/19952 A1 | 3/2002 |
| WO | 03/105673 A2 | 12/2003 |
| WO | 2014/133755 A1 | 9/2014 |

(56) References Cited

FOREIGN PATENT DOCUMENTS

WO     2017/168208 A1    10/2017
WO     2018049227 A1    3/2018

OTHER PUBLICATIONS

International Search Report and Written Opinion for Application No. PCT/US2019/019060, dated Jun. 5, 2019.
International Search Report and Written Opinion, PCT/IB2020/000932, dated Jul. 29, 2021.
International Search Report and Written Opinion, PCT/IB2020/000942, dated Aug. 10, 2021.

* cited by examiner

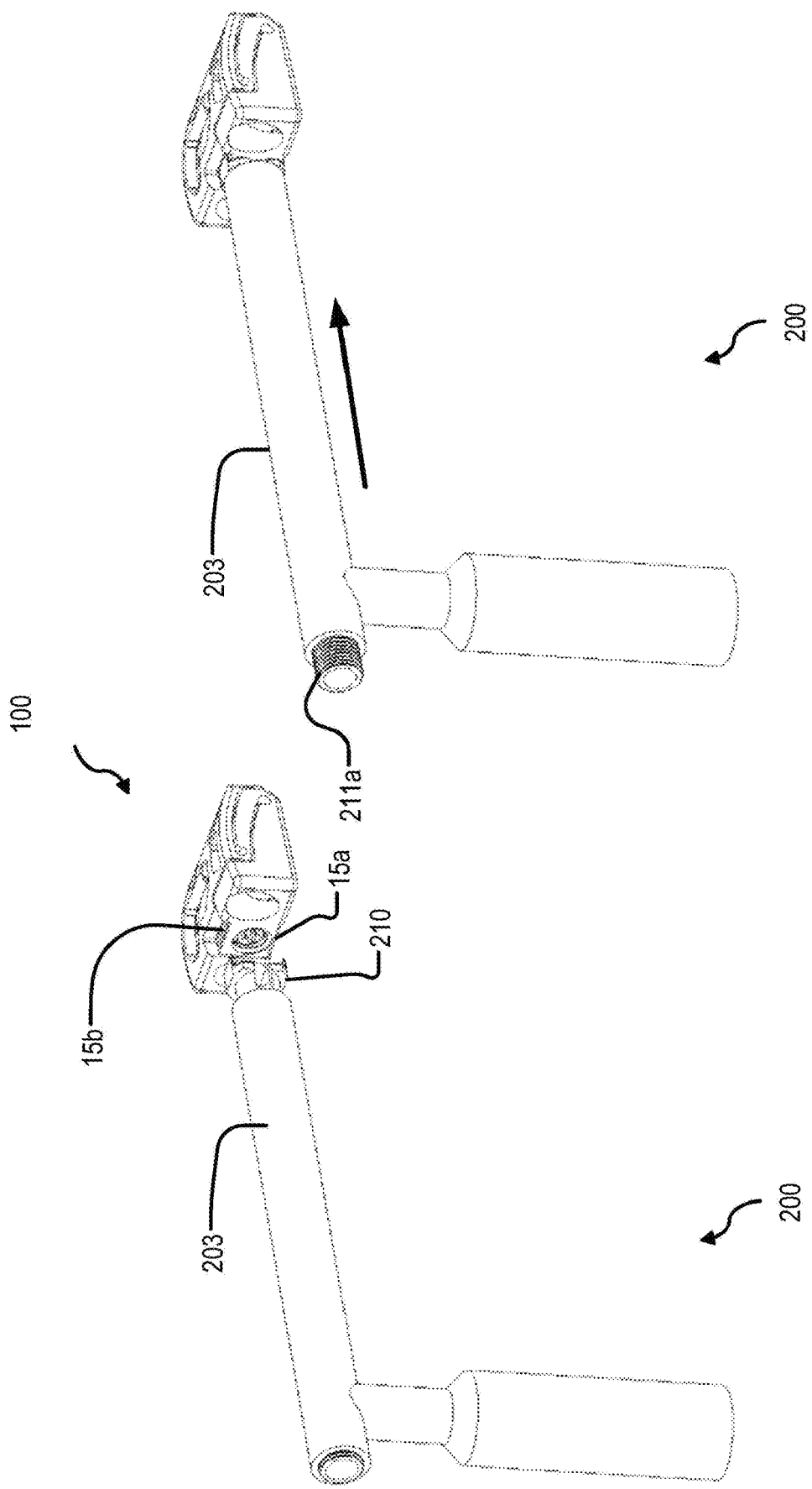

100

UNIBODY DUAL EXPANDING INTERBODY IMPLANT

FIELD

The present technology is generally related to a unibody expanding interbody implant for use in a medical procedure related to the spine. In some embodiments, disclosed implants may be used in an anterior cervical discectomy and fusion (ACDF) procedure although other uses in other areas of the spine and other surgical approaches and procedures are also contemplated.

BACKGROUND

Mechanically operated interbody implants may be used to align and/or realign a patient's spine during a medical procedure. Conventional implants designed for the Thoracic and Lumbar region of the spine often include top and bottom endplates and a mechanical means to separate the top and bottom endplates. The mechanical mechanisms to separate the top and bottom endplates are often cumbersome and require a large footprint that is often unsuitable for ACDF type surgeries of the cervical portion of the spine.

SUMMARY

The techniques of this disclosure generally relate to a implant that is independently expandable at a first side and a second side opposite the first side, and preferably, for example, such an implant having a unibody construction.

In one aspect, the present disclosure provides a unibody implant movable between an expanded position and a contracted position may be disclosed. The unibody implant may include a unitary expandable body extending from a proximal side to a distal side in a longitudinal direction, extending from a first lateral side to a second lateral side in a lateral direction, and extending from a superior side to an inferior side in a vertical direction, for example. In various embodiments, the unitary expandable body may be defined by an inferior portion, a superior portion, and a medial portion, for example. The inferior portion may be connected to the medial portion and the medial portion may be connected to the superior portion, for example. The unibody implant may include a first set screw and a second set screw rotatably supported by the body and rotatable in a clockwise direction and counterclockwise direction around a rotation axis that extends parallel to the longitudinal direction, for example. In various embodiments, the first set screw may have a first inclined surface facing the proximal side and the second set screw may have a second inclined surface facing the distal side, for example. In various embodiments the medial portion may include a first inclined ramp disposed on an interior surface thereof and facing the first inclined surface of the first set screw, for example. Additionally, the superior portion may include a second inclined ramp disposed on an interior surface thereof and facing the second inclined surface of the second set screw, for example. The first set screw may be movable in the longitudinal direction towards the proximal side or away from the proximal side upon rotation of the first set screw along the rotation axis and the second set screw may be movable in the longitudinal direction towards the distal side and away from the distal side upon rotation of the second set screw along the rotation axis, for example. In various embodiments, in an unexpanded position, the first set screw and second set screw are disposed in a medial position with respect to the proximal side and distal side, for example Additionally, in a first expanded position, the first set screw is disposed proximate the proximal side relative to the unexpanded position and the first inclined surface of the first set screw supports the first inclined ramp such that a vertical distance of the body between the superior and inferior sides of the body adjacent the proximal side of the body is greater than in the unexpanded position, for example. Furthermore, in a second expanded position, the second set screw is disposed proximate the distal side relative to the unexpanded position and the second inclined surface of the second set screw supports the second inclined ramp such that a vertical distance of the body between the superior and inferior sides of the body adjacent the distal side of the body is greater than in the unexpanded position, for example.

In various embodiments, the inferior portion may include a first threaded aperture rotatably supporting the first set screw and a second threaded aperture rotatably supporting the second set screw, for example.

In various embodiments, the inferior portion may include a first threaded aperture rotatably supporting the first set screw and a second threaded aperture rotatably supporting a first portion of the second set screw, and the superior portion may include a third threaded aperture rotatably supporting a second portion of the second set screw, for example.

In various embodiments, the first inclined surface may be conically shaped and the second inclined surface may be conically shaped, for example.

In various embodiments, the first inclined ramp may include a first curved surface extending towards the first lateral side and second lateral side that tapers towards the proximal end, the first curved surface may be frictionally engaged with the first inclined surface of the first set screw, for example Additionally, the second inclined ramp may include a second curved surface extending towards the first lateral side and second lateral side that tapers towards the distal side, the second curved surface may be frictionally engaged with the second inclined surface of the second set screw, for example.

In various embodiments, the inferior portion may be connected to the medial portion by the first lateral side and second lateral side proximate the distal side such that a first lateral seam may be formed as a first discontinuity on the first lateral side between the inferior portion and the medial portion and a second lateral seam may be formed as a second discontinuity on the second lateral side between the inferior portion and the medial portion, for example.

In various embodiments, the first discontinuity may include a first teardrop cutout proximate the distal side and the second discontinuity may include a second teardrop cutout proximate the distal side, for example.

In various embodiments, the medial portion may be connected to the superior portion by the first lateral side and second lateral side proximate the proximal side such that a third lateral seam may be formed as a third discontinuity on the first lateral side between the medial portion and superior portion and a fourth lateral seam may be formed as a fourth discontinuity on the second lateral side between the medial portion and superior portion, for example.

In various embodiments, the third discontinuity may include a third teardrop cutout proximate the proximal side and the second discontinuity may include a fourth teardrop cutout proximate the proximal side.

In various embodiments, the inferior portion may be connected to the medial portion by the first lateral side and second lateral side proximate the distal side such that a first lateral seam may be formed as a first discontinuity on the first lateral side between the inferior portion and the medial portion and a second lateral seam may be formed as a second discontinuity on the second lateral side between the inferior portion and the medial portion, for example. In various embodiments, the medial portion may be connected to the superior portion by the first lateral side and second lateral side proximate the proximal side such that a third lateral seam may be formed as a third discontinuity on the first lateral side between the medial portion and superior portion and a fourth lateral seam may be formed as a fourth discontinuity on the second lateral side between the medial portion and superior portion, for example.

In various embodiments, the first discontinuity may include a first teardrop cutout proximate the distal side and the second discontinuity may include a second teardrop cutout proximate the distal side, and the third discontinuity may include a third teardrop cutout proximate the proximal side and the second discontinuity may include a fourth teardrop cutout proximate the proximal side, for example.

In various embodiments, the proximal side may be defined by a first vertical surface of the inferior portion and a second vertical surface of the medial portion, for example.

In various embodiments, the first vertical surface may include an access aperture providing access to the first set screw and the second set screw, for example.

In various embodiments, the inferior portion may include a first bone screw aperture extending from the first vertical surface of the inferior portion and through a bottom surface of the inferior portion, the first bone screw aperture defining a first bone screw trajectory projecting towards the distal side that may be inclined with respect to the bottom surface of the inferior portion, for example.

In various embodiments, the second vertical surface may include a second bone screw aperture extending from the second vertical surface of the medial portion and through a top surface of the superior portion, the second bone screw aperture defining a second bone screw trajectory projecting towards the distal side that may be inclined with respect to the top surface of the superior portion, for example.

In various embodiments, the first set screw may include a first hollow interior including a first circumferential interior surface may have a first plurality of projections and valleys and the second set screw may include a second hollow interior including a second circumferential interior surface may have a second plurality of projections and valleys, for example.

In various embodiments, the first set screw and second set screw are coaxially aligned, for example.

In various embodiments, the first set screw and second set screw comprise a coaxially aligned hollow interior including a plurality of projections and valleys, respectively.

In another aspect, the disclosure provides for a system for expanding and contracting a unibody implant. The system may include a unibody implant movable between an expanded position and a contracted position may be disclosed. The unibody implant may include a unitary expandable body extending from a proximal side to a distal side in a longitudinal direction, extending from a first lateral side to a second lateral side in a lateral direction, and extending from a superior side to an inferior side in a vertical direction, for example. In various embodiments, the unitary expandable body may be defined by an inferior portion, a superior portion, and a medial portion, for example. The inferior portion may be connected to the medial portion and the medial portion may be connected to the superior portion, for example. The unibody implant may include a first set screw and a second set screw rotatably supported by the body and rotatable in a clockwise direction and counterclockwise direction around a rotation axis that extends parallel to the longitudinal direction, for example. In various embodiments, the first set screw may have a first inclined surface facing the proximal side and the second set screw may have a second inclined surface facing the distal side, for example. In various embodiments the medial portion may include a first inclined ramp disposed on an interior surface thereof and facing the first inclined surface of the first set screw, for example Additionally, the superior portion may include a second inclined ramp disposed on an interior surface thereof and facing the second inclined surface of the second set screw, for example. The first set screw may be movable in the longitudinal direction towards the proximal side or away from the proximal side upon rotation of the first set screw along the rotation axis and the second set screw may be movable in the longitudinal direction towards the distal side and away from the distal side upon rotation of the second set screw along the rotation axis, for example. In various embodiments, movement of the first set screw in the longitudinal direction towards the proximal side urges the first inclined surface against the first inclined ramp thereby expanding a vertical distance of the body between the superior and inferior sides of the body adjacent the proximal side of the body, and movement of the second set screw in the longitudinal direction towards the distal side urges the second inclined surface against the second inclined ramp thereby expanding a vertical distance of the body between the superior and inferior sides of the body adjacent the distal side of the body, for example. Furthermore, the first set screw may include a first hollow interior including a first circumferential interior surface may have a first plurality of projections and valleys and the second set screw may include a second hollow interior including a second circumferential interior surface may have a second plurality of projections and valleys, for example. The system may include an inserter that may have a rotatable drive end extending at least a first distance in a longitudinal direction corresponding to a length of the first circumferential interior surface, the rotatable drive end may have a third plurality of projections and valleys corresponding in size and shape to the first plurality of projections and valleys, for example. In various embodiments, the inserter may be configured to rotate either one of the first set screw and second set screw at a time, and/or both of the first set screw and second set screw at the same time. In another aspect, the present disclosure provides for a method for expanding and contracting a unibody implant. The method may include providing a system for expanding and contracting a unibody implant. The system may include a unibody implant movable between an expanded position and a contracted position may be disclosed. The unibody implant may include a unitary expandable body extending from a proximal side to a distal side in a longitudinal direction, extending from a first lateral side to a second lateral side in a lateral direction, and extending from a superior side to an inferior side in a vertical direction, for example. In various embodiments, the unitary expandable body may be defined by an inferior portion, a superior portion, and a medial portion, for example. The inferior portion may be connected to the medial portion and the medial portion may be connected to the superior portion, for example. The unibody implant may include a first set screw and a second set screw rotatably supported by the body and rotatable in a clockwise direction and counterclockwise direction around a rotation axis that extends parallel to the longitudinal direction, for example. In various embodiments, the first set screw may have a first inclined surface facing the proximal side and the second set screw may have a second inclined surface facing the distal side, for example. In various embodiments the medial portion may include a first inclined ramp disposed on an interior surface thereof and facing the first inclined surface of the first set screw, for example Additionally, the superior portion may include a second inclined ramp disposed on an interior surface thereof and facing the second inclined surface of the second set screw, for example. The first set screw may be movable in the longitudinal direction towards the proximal side or away from the proximal side upon rotation of the first set screw along the rotation axis and the second set screw may be movable in the longitudinal direction towards the distal side and away from the distal side upon rotation of the second set screw along the rotation axis, for example. In various embodiments, movement of the first set screw in the longitudinal direction towards the proximal side urges the first inclined surface against the first inclined ramp thereby expanding a vertical distance of the body between the superior and inferior sides of the body adjacent the proximal side of the body, and movement of the second set screw in the longitudinal direction towards the distal side urges the second inclined surface against the second inclined ramp thereby expanding a vertical distance of the body between the superior and inferior sides of the body adjacent the distal side of the body, for example. Furthermore, the first set screw may include a first hollow interior including a first circumferential interior surface may have a first plurality of projections and valleys and the second set screw may include a second hollow interior including a second circumferential interior surface may have a second plurality of projections and valleys, for example. The system may include an inserter that may have a rotatable drive end extending at least a first distance in a longitudinal direction corresponding to a length of the first circumferential interior surface, the rotatable drive end may have a third plurality of projections and valleys corresponding in size and shape to the first plurality of projections and valleys, for example. In various embodiments, the inserter may be configured to rotate either one of the first set screw and second set screw at a time, and/or both of the first set screw and second set screw at the same time. The method may include the step of positioning the unibody implant in a cervical region of a patient between a superior vertebrae and an inferior vertebrae, for example. Additionally, the method may include causing at least one of a lordosis expansion by rotating the first set screw via the drive end of the inserter and a kyphosis expansion by rotating the second set screw via the drive end of the inserter, for example.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 11A is a perspective view of a surgical tool for use with disclosed unibody implants.

FIG. 11B is a perspective view of a surgical tool for use with disclosed unibody implants.

FIG. 28 is a reference drawing showing the human spine of which various disclosed implant embodiments may be installed in.

FIG. 29 is a reference drawing showing various planes and reference directions of which the various disclosed implant embodiments may move in or act in.

DETAILED DESCRIPTION

Figure 1:
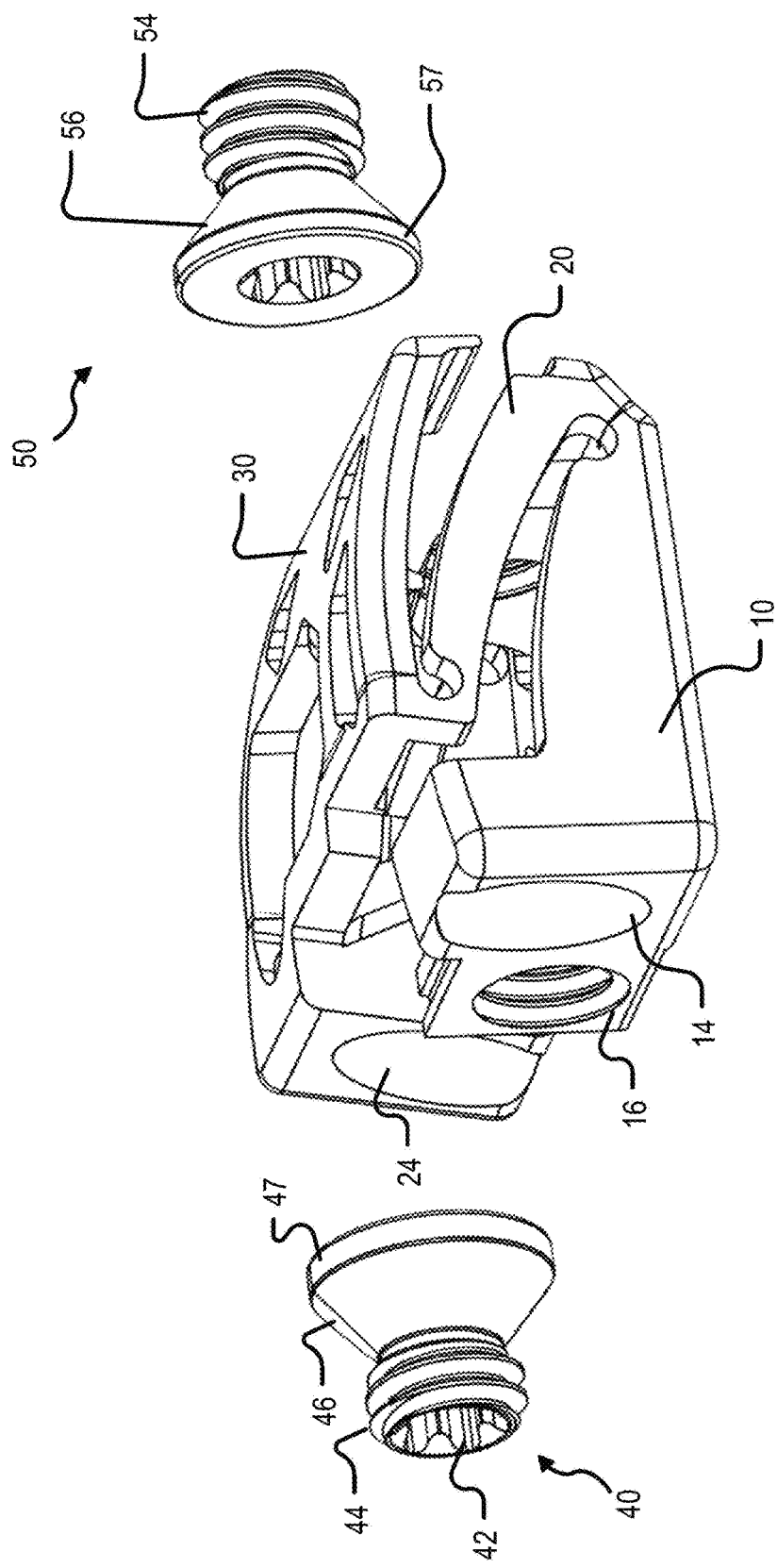
FIG. 1 is an exploded parts view of a unibody implant.

Embodiments of the present disclosure relate generally, for example, to spinal stabilization systems, and more particularly, to surgical instruments for use with spinal stabilization systems. Embodiments of the devices and methods are described below with reference to the Figures.

The following discussion omits or only briefly describes certain components, features and functionality related to medical implants, installation tools, and associated surgical techniques, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context or other statements clearly indicate otherwise.

Terms such as "same," "equal," "planar," "coplanar," "parallel," "perpendicular," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise.

Referring generally to FIGS. 1-23, an example unibody expandable implant 100 and a corresponding surgical tool 200 are disclosed. The unibody implant 100 may be used for an ACDF surgery in the cervical area of the spine (see FIG. 28), although other uses or approaches, including lateral, anterior, oblique, posterior lateral, anterolateral, transforaminal, etc., within the lumbar and/or thoracic area of the spine are also contemplated. The present disclosure aims, for example, to reduce the complexity of mechanical mechanisms to cause distraction, lordosis, and kyphosis while increasing the available interior space of an implant by minimizing the size of the moving mechanism that causes distraction, lordosis, and kyphosis. At least one advantage of minimizing the size of the moving mechanism is that a relatively greater volume of a bone growth promoting material may be placed and/or injected inside of the implant for promoting fusion between adjacent vertebrae of a patient.

Figure 2:
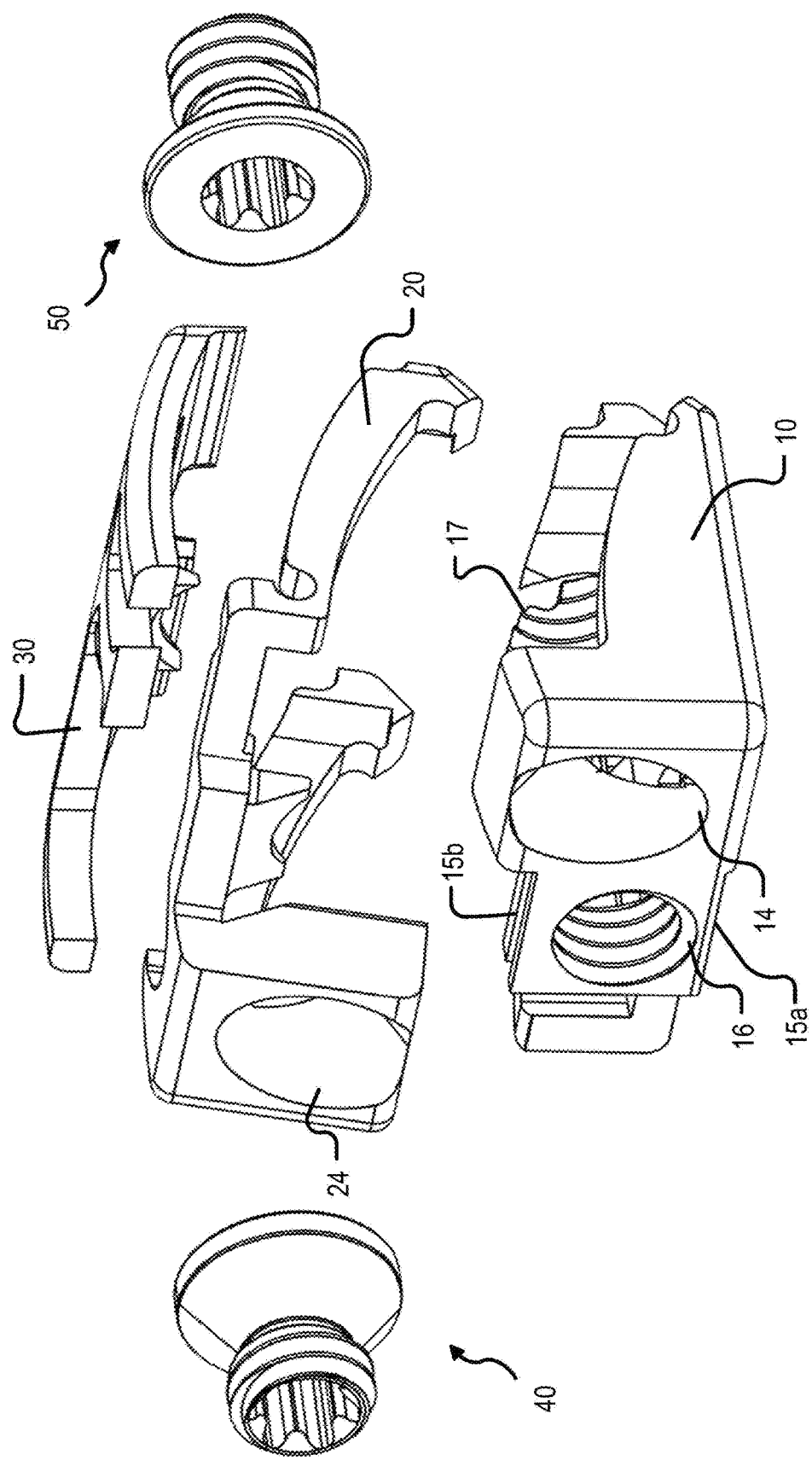
FIG. 2 is an alternate exploded parts view of a unibody implant.
Figure 3:
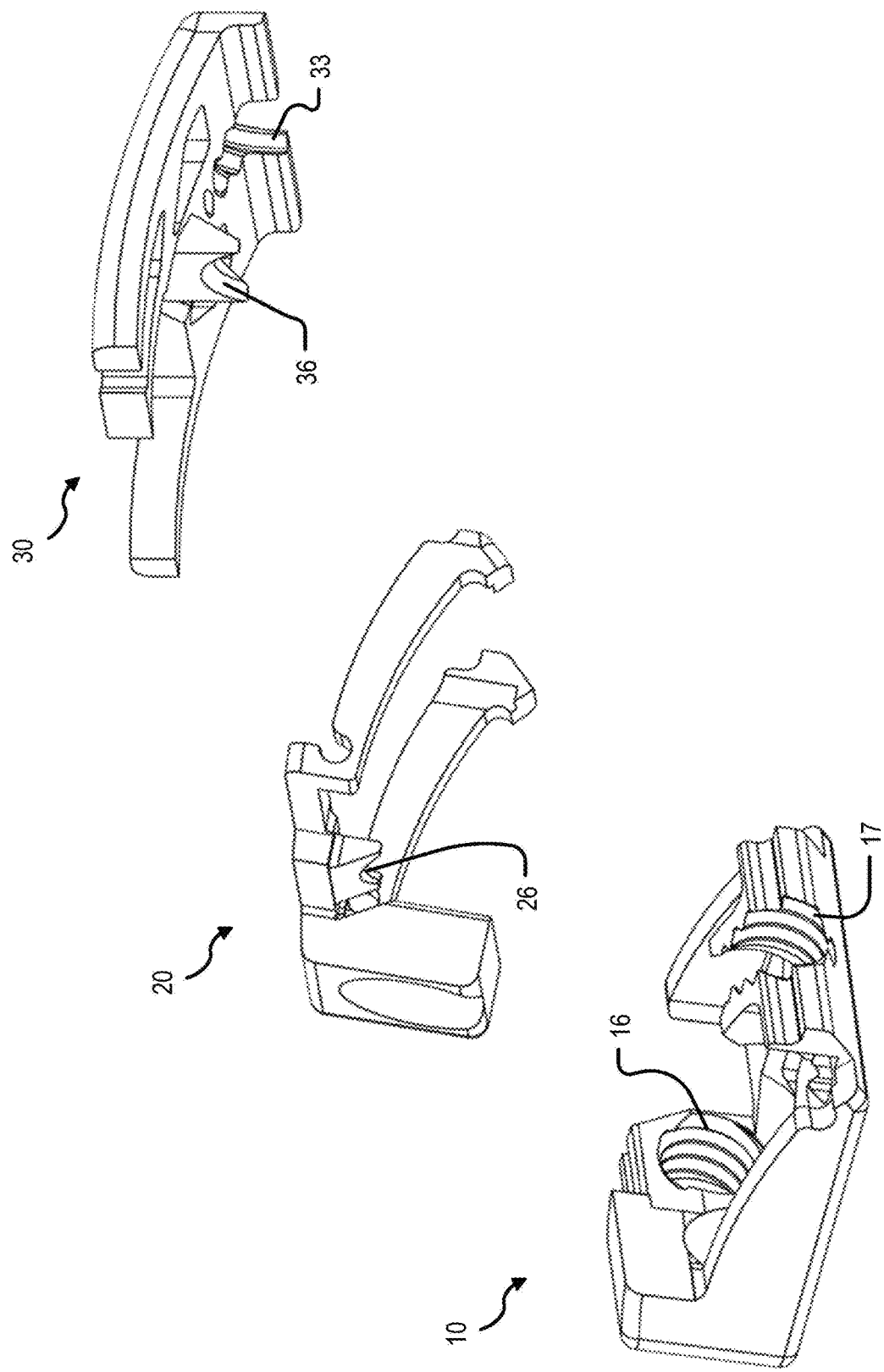
FIG. 3 is an explode parts view of a body portion of a unibody implant.

FIGS. 1-3 illustrate various exploded parts views of a unibody implant. In the example embodiment, a unibody implant 100 may include an inferior portion 10, a medial portion 20, and a superior portion 30 that define the outside surfaces of unibody implant 100. It shall be understood that although unibody implant 100 is described herein as being composed of an inferior portion 10, a medial portion 20, and a superior portion 30 that these portions are securely connected to one another, or are in the form of a single monolithic unitary part, to form a unibody implant 100. For example, the inferior portion 10 is connected to the medial portion 20 and the medial portion is connected to the superior portion 30. In various embodiments, the unibody implant 100 is expandable between a contracted position and an expanded position by movement of a first set screw 40 and/or a second set screw 50. For example, the first set screw 40 may be referred to as an anterior set screw and the second set screw 50 may be referred to as a posterior set screw and each may adjust a relative height of the implant in the sagittal plane although the particular orientation of the implant 100 may be different when installed within an intervertebral disc space of a patient 1 (see FIG. 29) and adjustment in the coronal plane is also contemplated.

In various embodiments, the first set screw 40 may include a drive feature 42 including a plurality of peaks and valleys disposed on an interior circumferential surface, a thread pattern 44 disposed on an exterior circumferential surface, and an inclined surface 46 facing the thread pattern 44. The inclined surface 46 may have a conical shape terminating at a smooth rim portion 47, for example. Similarly, in various embodiments, the second set screw 50 may include a drive feature 52 including a plurality of peaks and valleys disposed on an interior circumferential surface, a thread pattern 54 disposed on an exterior circumferential surface, and an inclined surface 56 facing the thread pattern 54. The inclined surface 56 may have a conical shape terminating at a smooth rim portion 57, for example.

In various embodiments, the first set screw 40 may be rotatably engaged with a first threaded aperture 16 of the inferior portion 10 and the second set screw 50 may be rotatably engaged with a second threaded aperture 17 of the inferior portion 10, for example. In various embodiments, the second threaded aperture 17 may include a discontinuity that is small enough such that the second set screw 50 may still be retained therein. For example, the discontinuity is less than a cross sectional width of the second set screw 50. Additionally, in various embodiments, the superior portion 30 may include a third threaded aperture 33 that enables second set screw 50 to rotatably engage both the second threaded aperture 17 and third threaded aperture 33 (at least in some collapsed positions). As will be explained in further detail below, an interior of the medial portion 20 may include a first inclined ramp 26 of which the inclined surface 46 of the first set screw 40 may act against. For example, when rotating the first set screw 40 it may move forward and backward within the first threaded aperture 16 thereby urging the inclined surface 46 of first set screw 40 against the first inclined ramp 26 to thereby expand a vertical height of the implant 100. Similarly, an interior of the superior portion 30 may include a second inclined ramp 36 of which the inclined surface 56 of the second set screw 50 may act against. For example, when rotating the second set screw 50 it may move forward and backward within the second threaded aperture 17 thereby urging the inclined surface 56 of second set screw 50 against the second inclined ramp 36 to thereby expand a vertical height of the implant 100.

Figure 4:
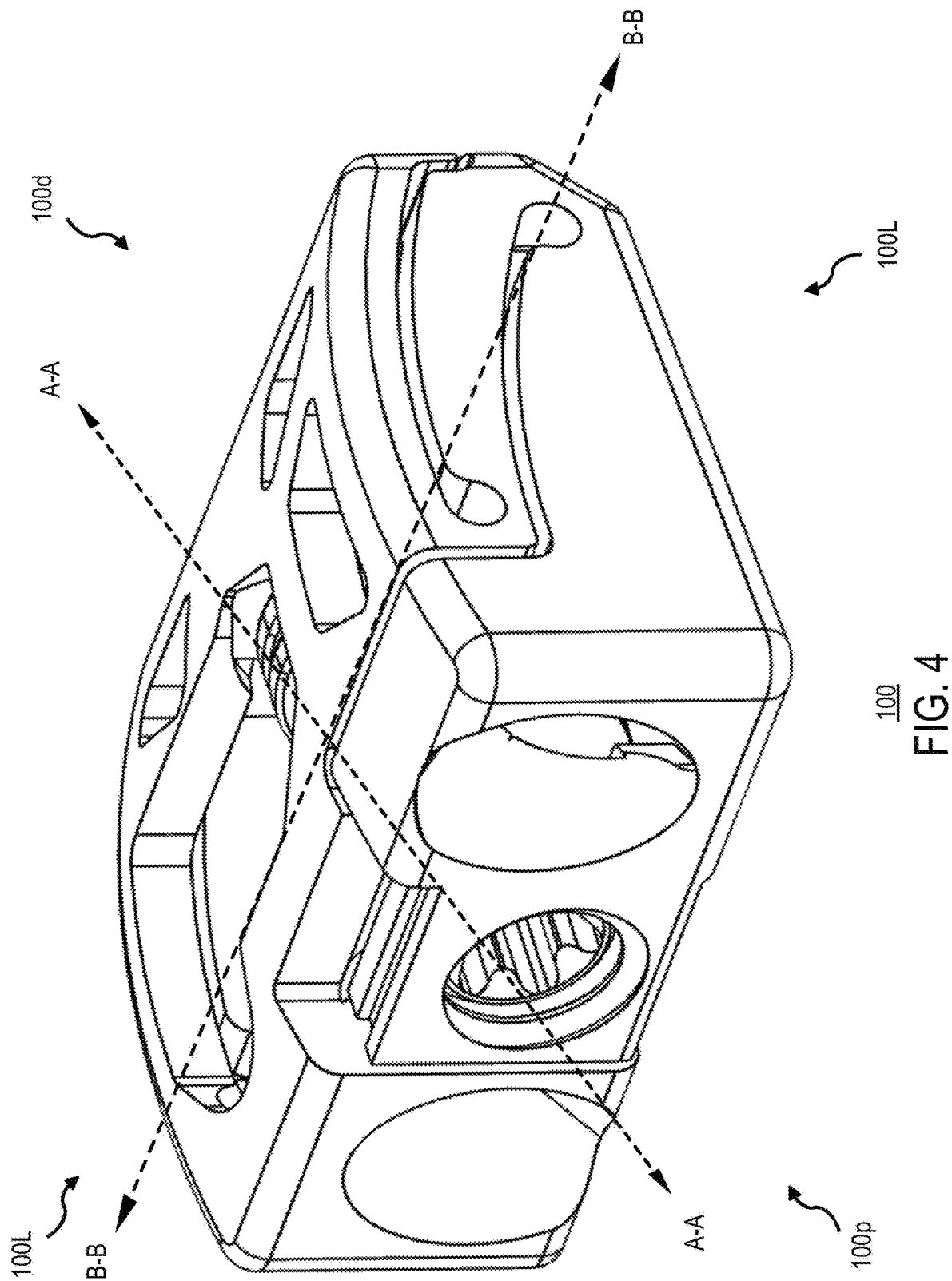
FIG. 4 is a perspective view of a unibody implant.
Figure 5:
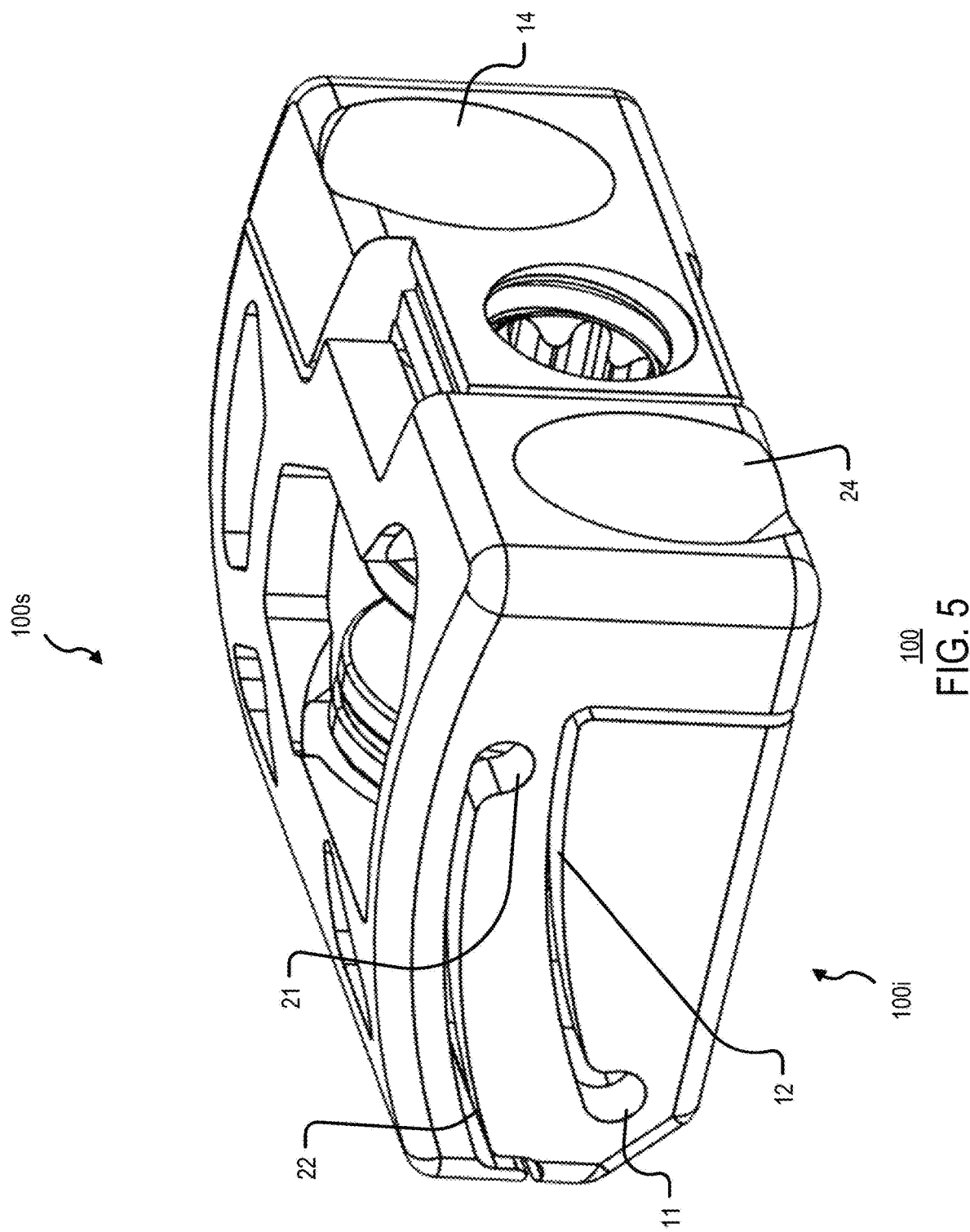
FIG. 5 is an alternate perspective view of a unibody implant.
Figure 6:
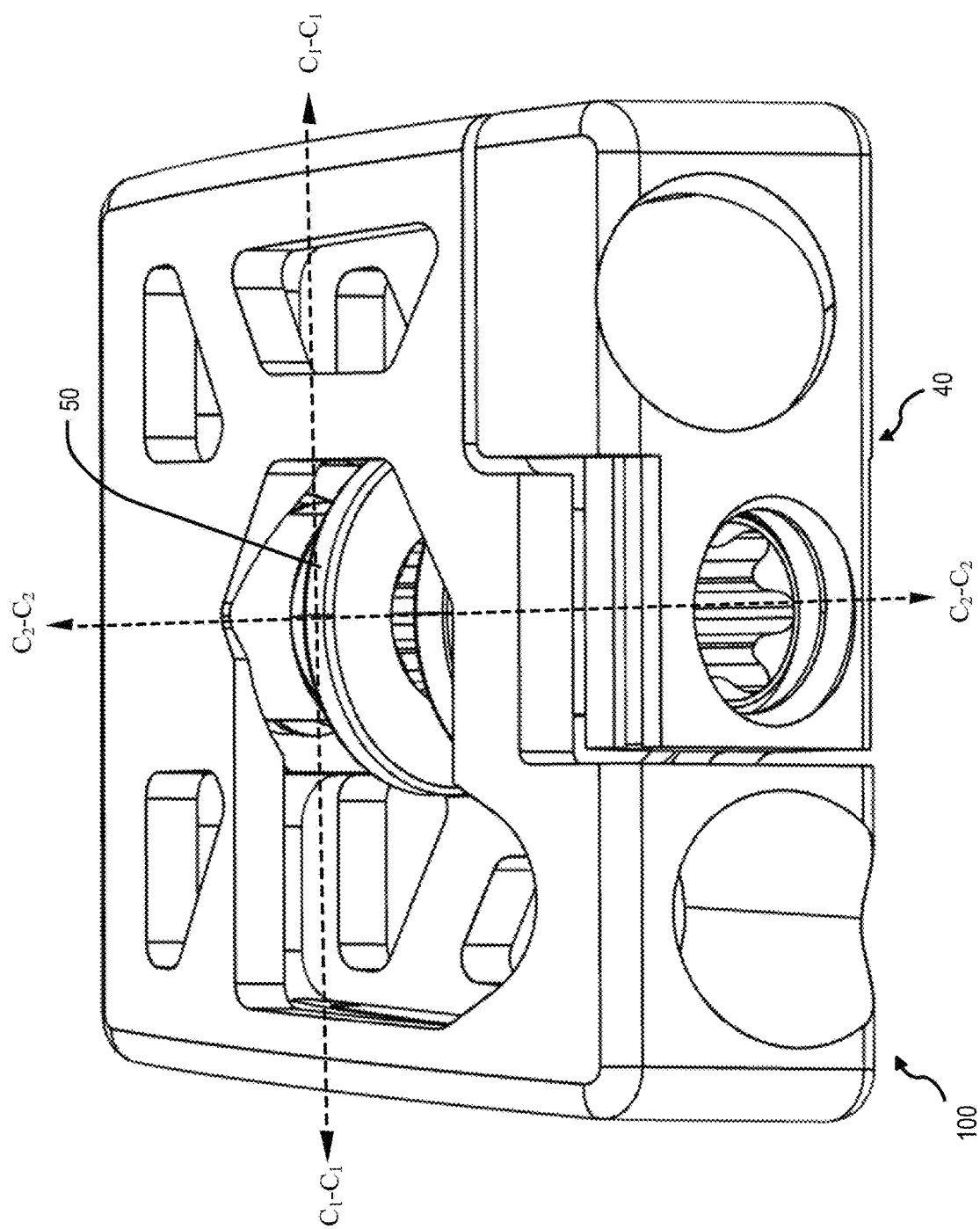
FIG. 6 is a top down front view of a unibody implant.

FIGS. 4 and 5 are perspective views of a unibody implant 100 and FIG. 6 is a front top down front view of a unibody implant 100. In the example embodiment, implant 100 may extend in a longitudinal direction along axis A-A from a proximal side 100$p$ to a distal side 100$d$. Implant 100 may extent in a lateral direction along axis B-B from a first lateral side 100$l$ to a second lateral side 100$l$, for example Additionally, implant 100 may include a superior side 100$s$ (top surface) and an inferior side 100$i$ (bottom surface). Referring to FIG. 5, implant 100 may include at least one bone screw aperture 14, 24. For example, the proximal side of implant 100 may include a first bone screw aperture 14 that extends through a vertical face of inferior portion 10 on the proximal side 100$p$ through the inferior side 100$i$. Additionally, the proximal side of implant 100 may include a second bone screw aperture 24 that extends through a vertical face of medial portion 20 on the proximal side 100$p$ through the superior side 100$s$. Implant 100 may include at least one seam 12, 22 on each lateral side 100$l$. For example, a first seam 12 may take the form of a discontinuity extending in the longitudinal direction along the first lateral surface 100$l$ between the inferior portion 10 and the medial portion 20, for example. The first seam 12 may include a teardrop cutout 11 proximate the distal side 100$d$ to facilitate the expansion of unibody implant 100, for example. Similarly, a second seam 22 may take the form of a discontinuity extending in the longitudinal direction along the first lateral surface 100$l$ between the medial portion 20 and the superior portion 30, for example. The second seam 22 may include a teardrop cutout 21 proximate the proximal side 100$p$, at least when viewed relative to teardrop cutout 11. Substantially the same seams 12, 22 and teardrop cutouts 11, 21 may be featured on both lateral sides 100*l* of implant 100. The seams 12, 22 and teardrop cutouts 11, 21 are configured to facilitate the expansion and contraction of unibody implant 100 while the inferior portion 10, medial portion 20, and superior portion 30 remain connected together. For example, the seams 12, 22 and teardrop cutouts 11, 21 facilitate the pivoting of the inferior portion 10, medial portion 20, and superior portion 30 relative to one another. FIG. 6 illustrates a top down front perspective view of implant 100 showing a first cross section $C_1$-$C_1$ extending in a lateral direction through the second set screw 50. FIG. 6 also illustrates a second cross section $C_2$-$C_2$ extending in a longitudinal direction through the center of implant 100 and passing through the center of the first set screw 40 and second set screw 50, for example.

Figure 7:
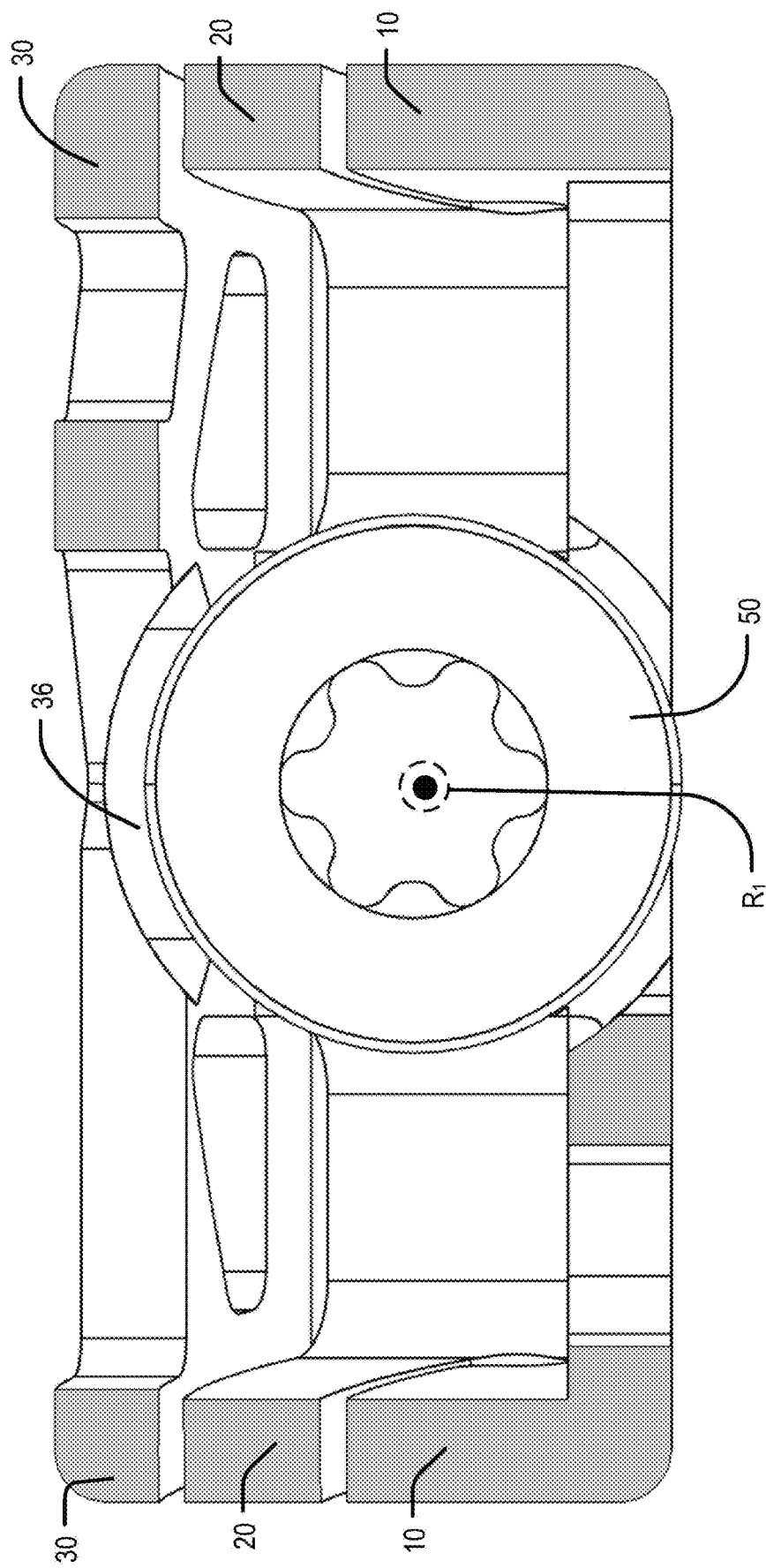
FIG. 7 is a cross section view taken along line $C_1$-$C_1$ of FIG. 6.
Figure 8:
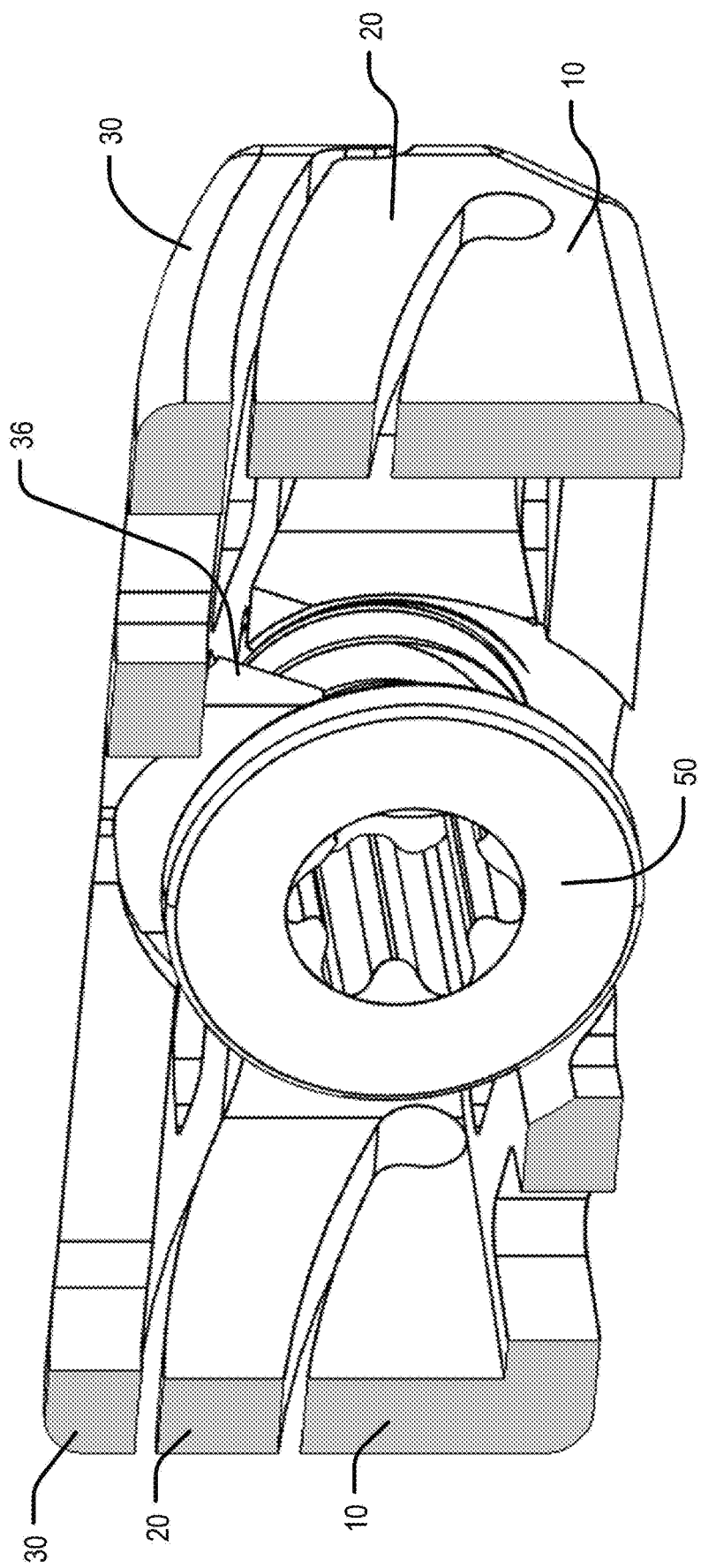
FIG. 8 is a perspective sectional view taken along line C1 of FIG. 6.

FIG. 7 is a cross section view taken along line $C_1$-$C_1$ of FIG. 6 and FIG. 8 is a perspective sectional view taken along line $C_1$-$C_1$ of FIG. 6. In the example embodiment, it is shown that a rotation axis $R_1$ extends through the center of second set screw 50, for example. Furthermore, the same rotation axis $R_1$ may extend through the first set screw 40 because the first and second set screws 40, 50 may be coaxially aligned. When rotating second set screw 50 clockwise or counterclockwise the second set screw 50 may move towards and away from the distal end 100*d* within the threaded aperture 17 of the inferior portion 10. In doing so, the inclined surface 56 of second set screw 50 may act against the inclined ramp 36 of the superior portion 30. For example, when the second set screw 50 is rotated such that it moves towards the distal end 100*d* the inclined surface 56 of second set screw 50 pushes against the inclined ramp 36 of the superior portion 30 thereby pushing the superior portion 30 upwards and away from the inferior portion 10. For example still, the inclined ramp 36 may have a conical shape or arcuate shaped geometry that tapers towards the distal side 100*d* of which the inclined surface 56 is nested within such that inclined surface 56 can frictionally push against and rotate within while the second set screw is advancing towards the distal end 100*d*. Furthermore, due to seams 22 and teardrop shaped cutout 21 on each lateral side surface 100*l* the superior portion may pivot upward and away from the inferior portion 10 at the distal side 100*d*. It shall be understood that the inclined surface 46 of first set screw 40 may act against the inclined ramp 26 in the same, substantially the same, and/or similar manner although towards the proximal end 100*p* as will be explained in further detail below.

Figure 9:
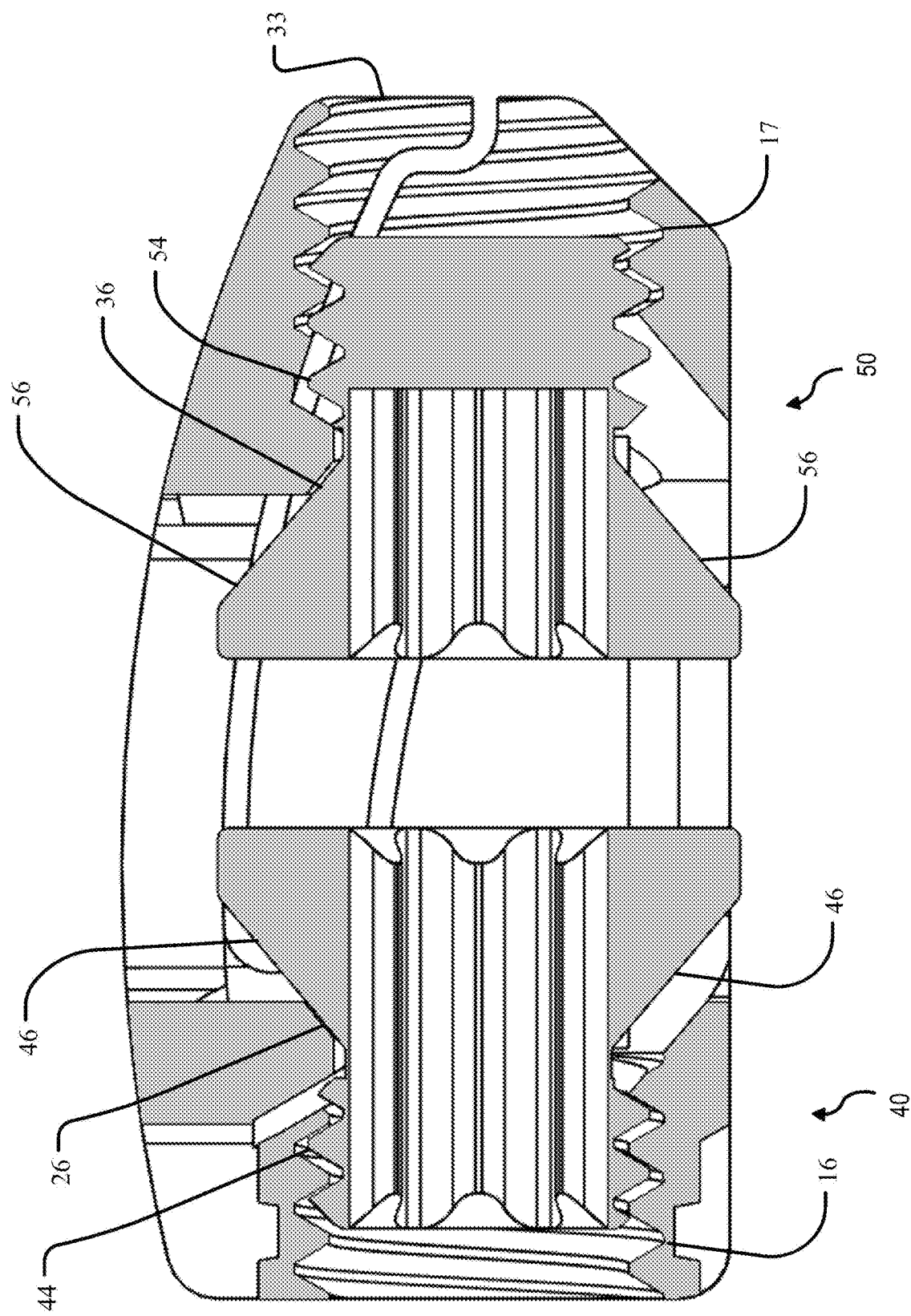
FIG. 9 is a cross section view taken along line $C_2$-$C_2$ of FIG. 6.
Figure 10:
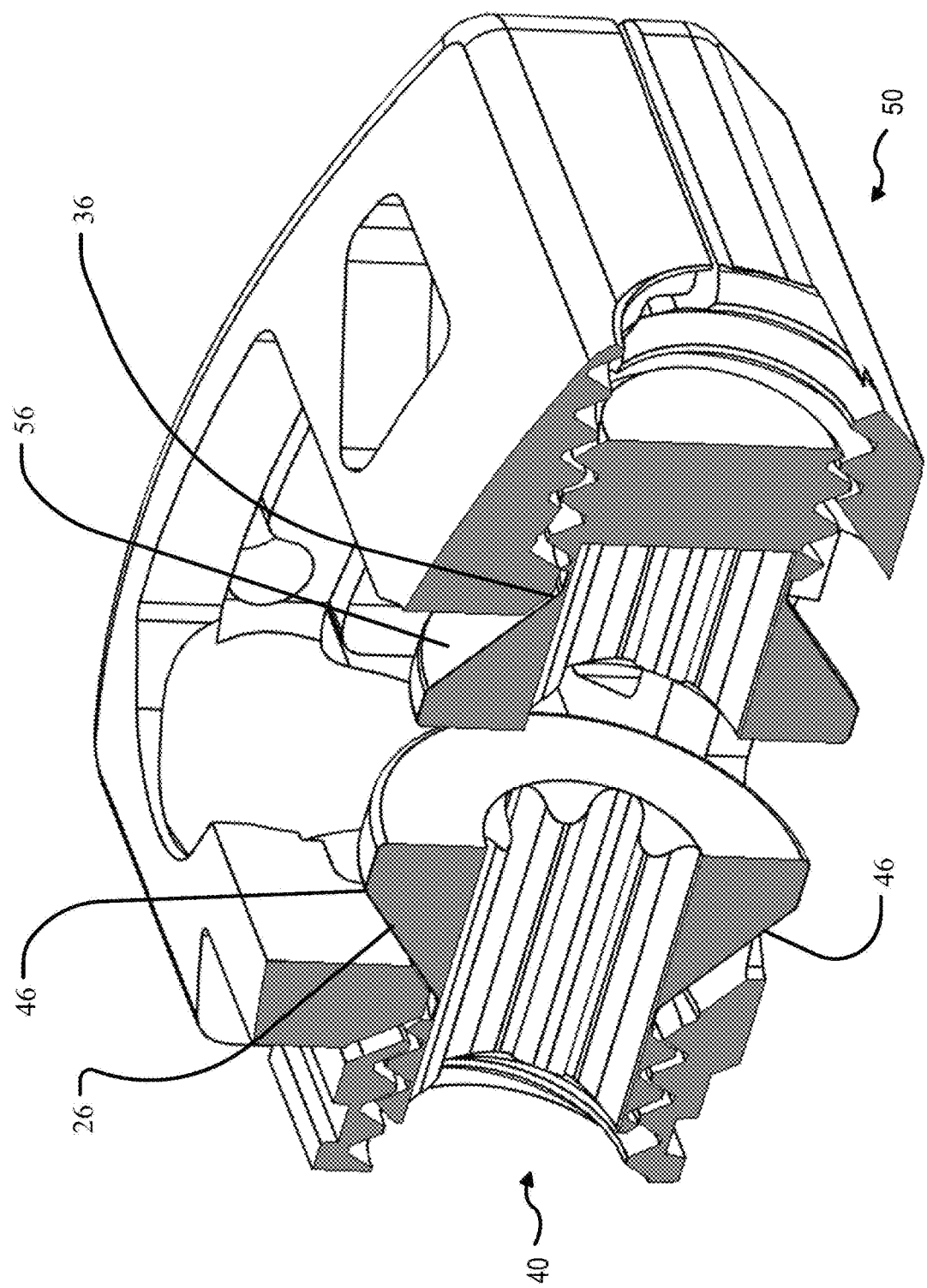
FIG. 10 is a perspective sectional view taken along line $C_2$-$C_2$ of FIG. 6.

FIG. 9 is a cross section view taken along line $C_2$-$C_2$ of FIG. 6 and FIG. 10 is a perspective sectional view taken along line $C_2$-$C_2$ of FIG. 6. In the example illustration, it is shown that the implant 100 is in a collapsed position, i.e., a non-expanded position. Each of the set screws 40, 50 are in a medial position towards the center of the implant 100. Consistent with the disclosure herein, as the first set screw 40 is rotated clockwise/counterclockwise it moves forward and backward within first threaded aperture 16. When rotating first set screw 40 clockwise or counterclockwise the first set screw 40 may move towards and away from the proximal end 100*p* within the threaded aperture 16 of the inferior portion 10. In doing so, the inclined surface 46 of first set screw 40 may act against the inclined ramp 26 of the medial portion 20. For example, when the first set screw 40 is rotated such that it moves towards the proximal end 100*p* the inclined surface 46 of first set screw 40 pushes against the inclined ramp 26 of the medial portion 20 thereby pushing the medial portion 20 upwards and away from the inferior portion 10. For example still, the inclined ramp 26 may have a conical shape or arcuate shaped geometry that tapers towards the proximal side 100*p* of which the inclined surface 46 is nested within such that inclined surface 46 can frictionally push against and rotate within inclined ramp 26 while the first set screw 40 is advancing towards the proximal end 100*p*.

Additionally, due to seams 12 and teardrop shaped cutout 11 on each lateral side surface 100*l* the medial portion may pivot upward and away from the inferior portion 10 at the proximal side 100*p*, for example. furthermore, in the example embodiment, the medial portion 20 defines a portion of the top of implant 100 proximate the proximal side 100*p* such that the top surface of implant 100 moves away from the inferior portion 10 and a vertical height of implant 100 is expanded at the proximal end 100*p*. Further still, those with skill in the art will recognize that the thread pitch of the first and second set screws 40, 50 and first, second, and third threaded apertures 16, 17, 33 may have a size and shape that corresponds to one another and the particular direction of any pitch may be adjusted such that either a counterclockwise rotation or a clockwise rotation may advance the relevant set screw 40, 50 towards the corresponding inclined ramp 26, 36. In at least one embodiment, the second set screw 50 is reverse threaded with respect to the first set screw 40, for example.

Figure 11C:
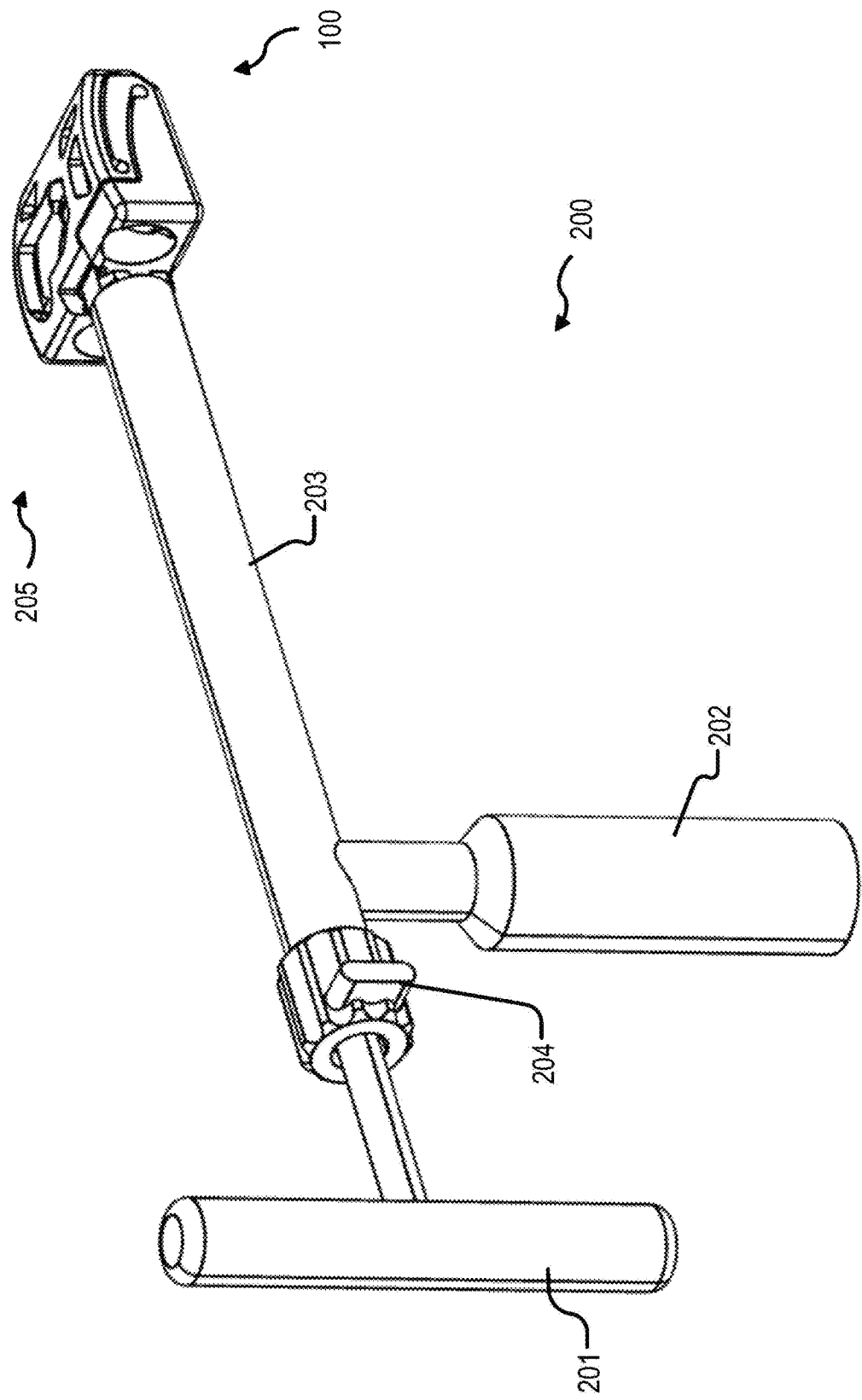
FIG. 11C is a perspective view of a surgical tool for use with disclosed unibody implants.

FIGS. 11A-11C are various perspective views of a surgical tool 200 for use with the various disclosed unibody implants 100. Surgical tool 200 may be an inserter type tool that can frictionally engage with implant 100 with a claw 210 or the like as shown in FIG. 11A. In other embodiments, surgical tool 200 or may engage with a dedicated inserter coupling portion via an outer sleeve portion at a distal end thereof. In the example embodiment, surgical tool 200 may frictionally engage implant 100 by expanding claw 210 such that it grasps engagement surfaces 15*a*, 15*b* (see also FIG. 2). Engagement surfaces 15*a*, 15*b* may include a groove extending in a direction between the first lateral end 100*l* and second lateral end 100*l*, for example. In some embodiments, an inner sleeve 211 of inserter 200 may engage with the threaded aperture 16 via corresponding threads. After claw 210 is engaged with the engagement surfaces 15*a*, 15*b* an outer sleeve 203 may slide forward (represented by arrows) to prevent claw 210 from opening up or loosening its grip with the engagement surfaces 15*a*, 15*b*, for example. In sliding the outer sleeve 203 forward a threaded end 211*a* of an inner sleeve 211 may become exposed at a proximal side of inserter 200, for example. A tightening knob 204 having a corresponding thread pattern to the threaded end 211 may be secured to the threaded end 211*a*. In some embodiments, by tightening the tightening knob 204 the claw 210 may further compress against and/or further secure the engagement surfaces 15*a*, 15*b*. As shown in FIG. 11C, a driver 201 having a drive end 205 (see FIG. 12) may be inserted within the hollow inner shaft 211 and extend through the threaded end 211*a* to the proximal side of inserter 200. Driver 201 may include a handle at the end for rotating the drive end 205 within the inner shaft 211 and a positioning handle 202 for an end user such as a surgeon to grasp or hold on to.

Figure 12:
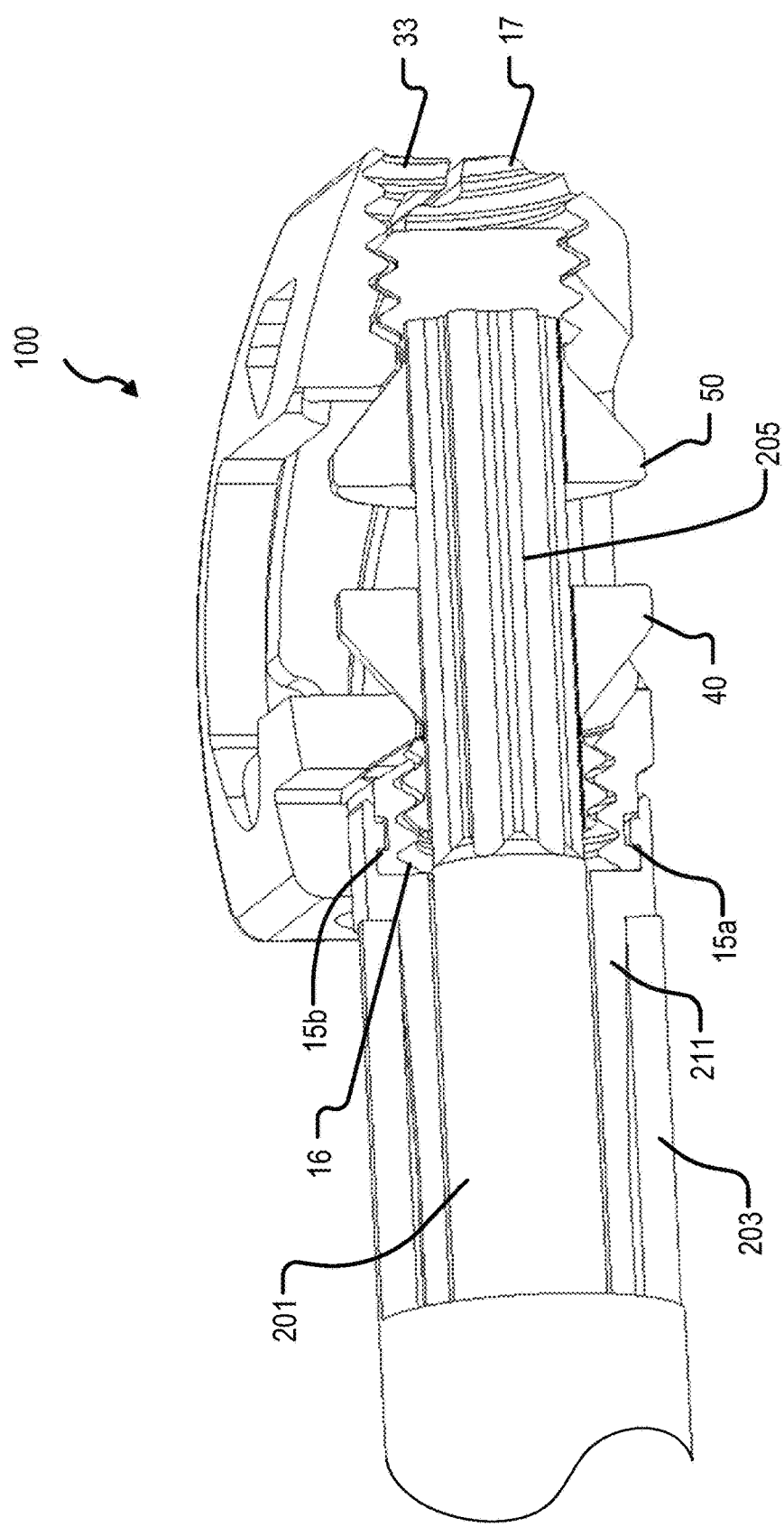
FIG. 12 is a cross section view showing a drive end of the surgical tool of FIG. 11 engaged with the first set screw and second set screw.

In various embodiments, the driver 201 may advance forward and backward freely or it may be secured via the tightening knob 204 with a latch, set screw, pin, etc. In a first tool position, the drive end 205 may engage the internal threads of both the first and second set screws 40, 50 at the same time and where the first and second set screws are axially aligned in the same position. For example, as shown in FIG. 12 each of the first and second set screw 40, 50 is engaged with the drive end 205 and rotation may cause a parallel distraction of the implant 100. In a second tool position, the drive end 205 may engage the internal threads of only the first set screw 40 and rotation may cause distraction at the proximal end 100p of implant (also referred to as anterior end). For example, by rotating only the first set screw 40 an inclination of the superior endplate 30 may be adjusted with respect to the inferior endplate 10 such that the top surface is inclined with respect to the bottom surface. In a third tool position, the tightening knob 204 may be used to keep the driver 201 in a position such that that the drive end 205 is passed through the first set screw 40 without engaging it and only engages the second set screw 50. In this way, by engaging only the second set screw 50 rotation of the drive end 205 may rotate the second set screw 50 to cause distraction at the distal end 100d of implant (also referred to as posterior end). For example, by rotating only the second set screw 50 an inclination of the superior endplate 30 may be adjusted with respect to the inferior endplate 10 such that the top surface is inclined with respect to the bottom surface in an opposite way with respect to the second tool position.

Figure 13:
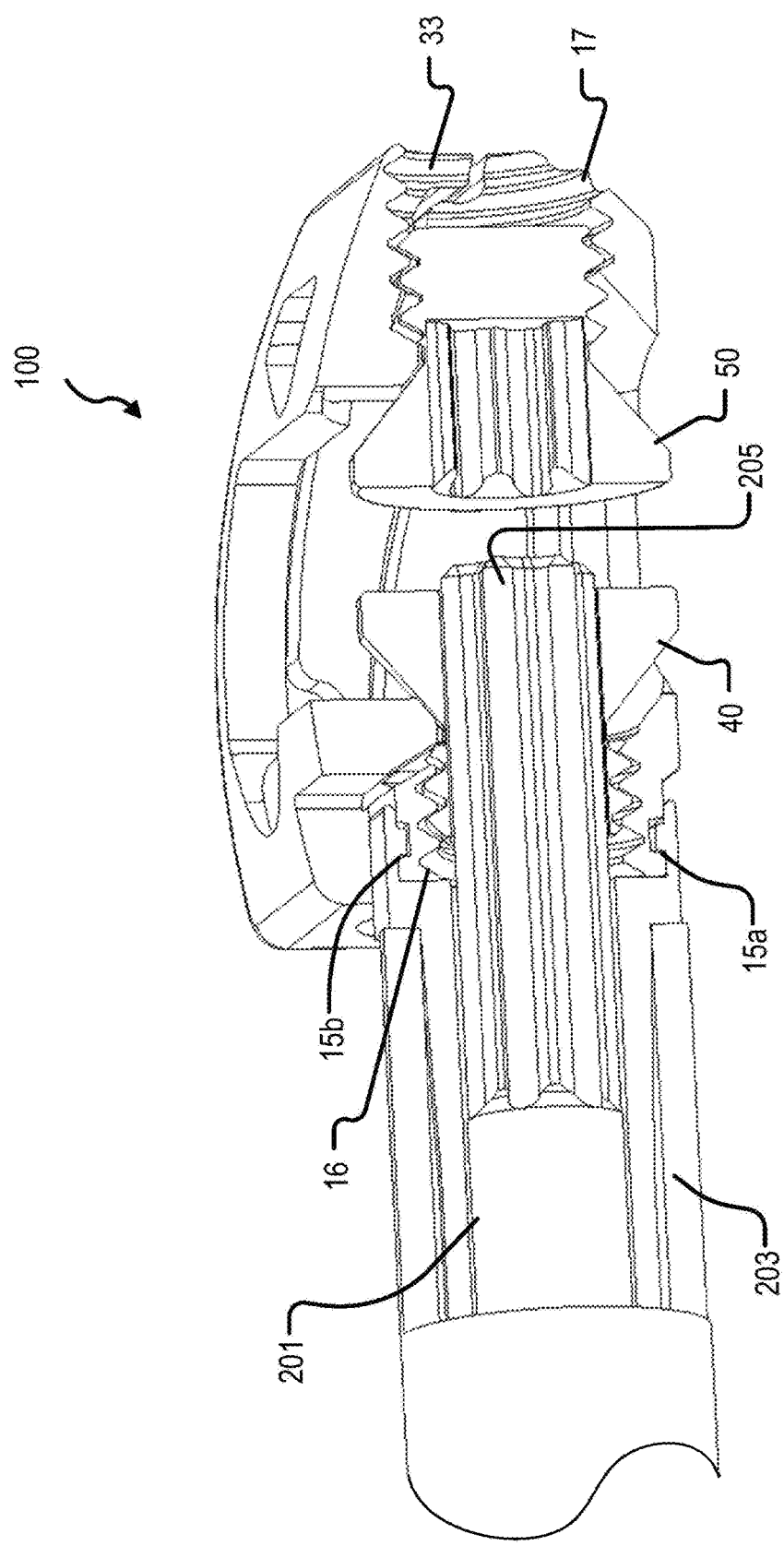
FIG. 13 is a cross section view showing a drive end of the surgical tool of FIG. 11 engaged with only the first set screw.
Figure 14:
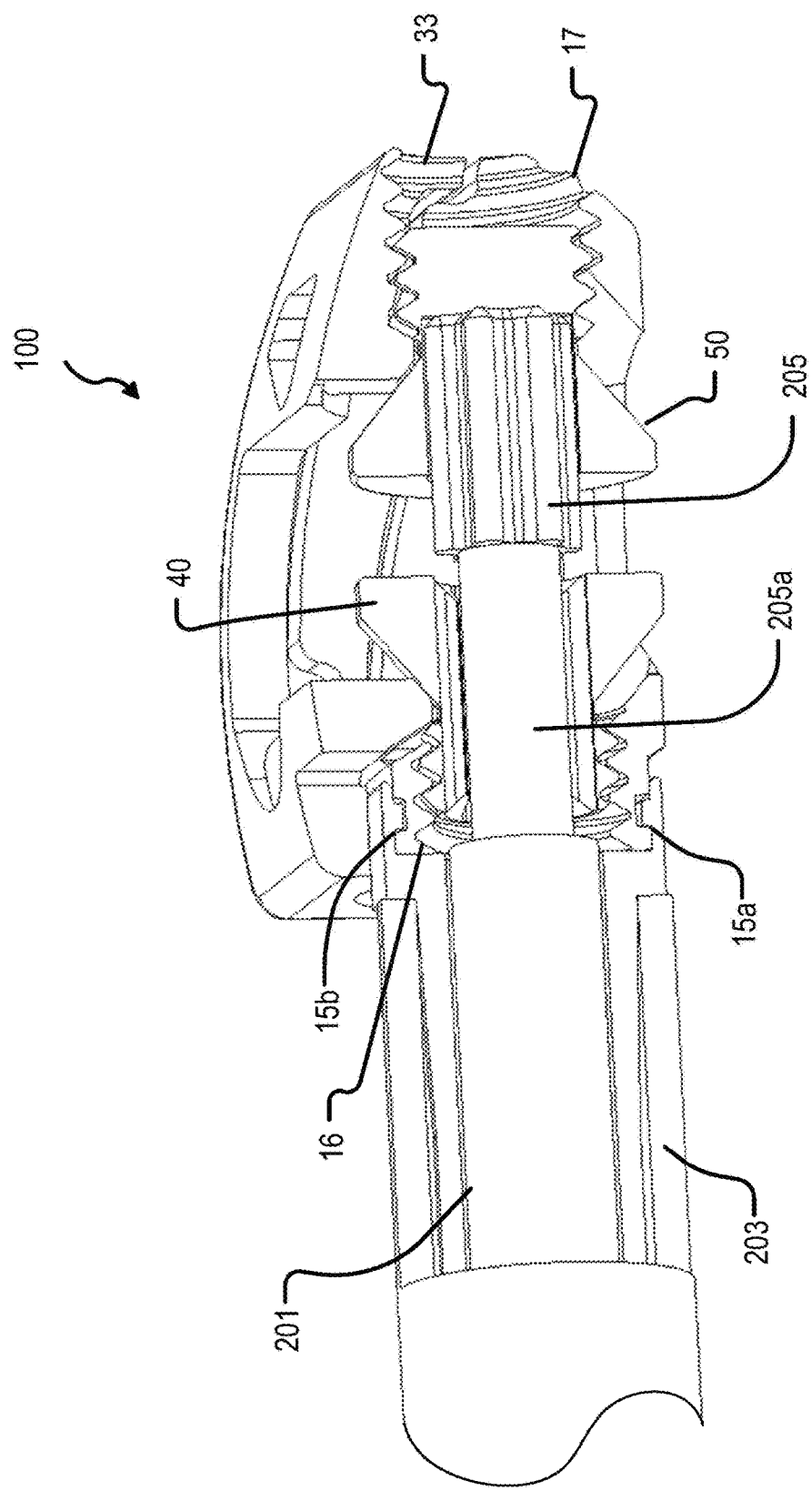
FIG. 14 is a cross section view showing a drive end of the surgical tool of FIG. 11 engaged with only the second set screw.

FIG. 12 is a cross section view showing a drive end 205 of the inserter 200 engaged with the first set screw 40 and second set screw 50. FIG. 13 is a cross section view showing a drive end 205 of the inserter 200 engaged with only the first set screw 40. FIG. 14 is a cross section view showing a drive end 205 of the surgical tool 200 engaged with only the second set screw 50. In the example embodiments, it is shown that the claw end 210 may remain engaged with engagement surfaces 15a, 15b while drive end 205 may engage with an internal circumferential drive surface of the first set screw 40 and/or second set screw 50. In various embodiments, the claw end 210 may comprise an outdented portion that may be seated within an indented portion of engagement surfaces 15a, 15b, for example. Additionally, drive end 205 may comprise a plurality of peaks and valleys or other drive features that have a size and shape generally corresponding to the plurality of peaks and valleys or other drive features of the internal circumferential surfaces of the first set screw 40 and second set screw 50, for example. For example, a hexolobular surface or the like. Because first set screw 40 and second set screw 50 are hollow, i.e., a passageway extends therethrough, the drive end 205 may reach either one of the first set screw 40 and second set screw 50 independently or even both simultaneously. For example, drive end 205 may have a length sufficiently long to rotate both first set screw 40 and second set screw 50 at the same time. Alternatively, drive end 205 may engage only one of first set screw 40 or second set screw 50 at a time. For example, as shown in FIG. 14 drive end 205 has a relatively shorter length in a longitudinal direction than in FIGS. 12 and 13 and includes a necked down portion 205a. The necked down portion 205a allows drive end 205 to extend through the first set screw 40 without engaging the first set screw 40 while engaging only the second set screw 50, for example. In this way, an end user may independently adjust a vertical height of implant 100 at either of the proximal side 100p and/or distal side 100d to achieve maximum range of flexibility in the configuration of implant 100.

Figure 15:
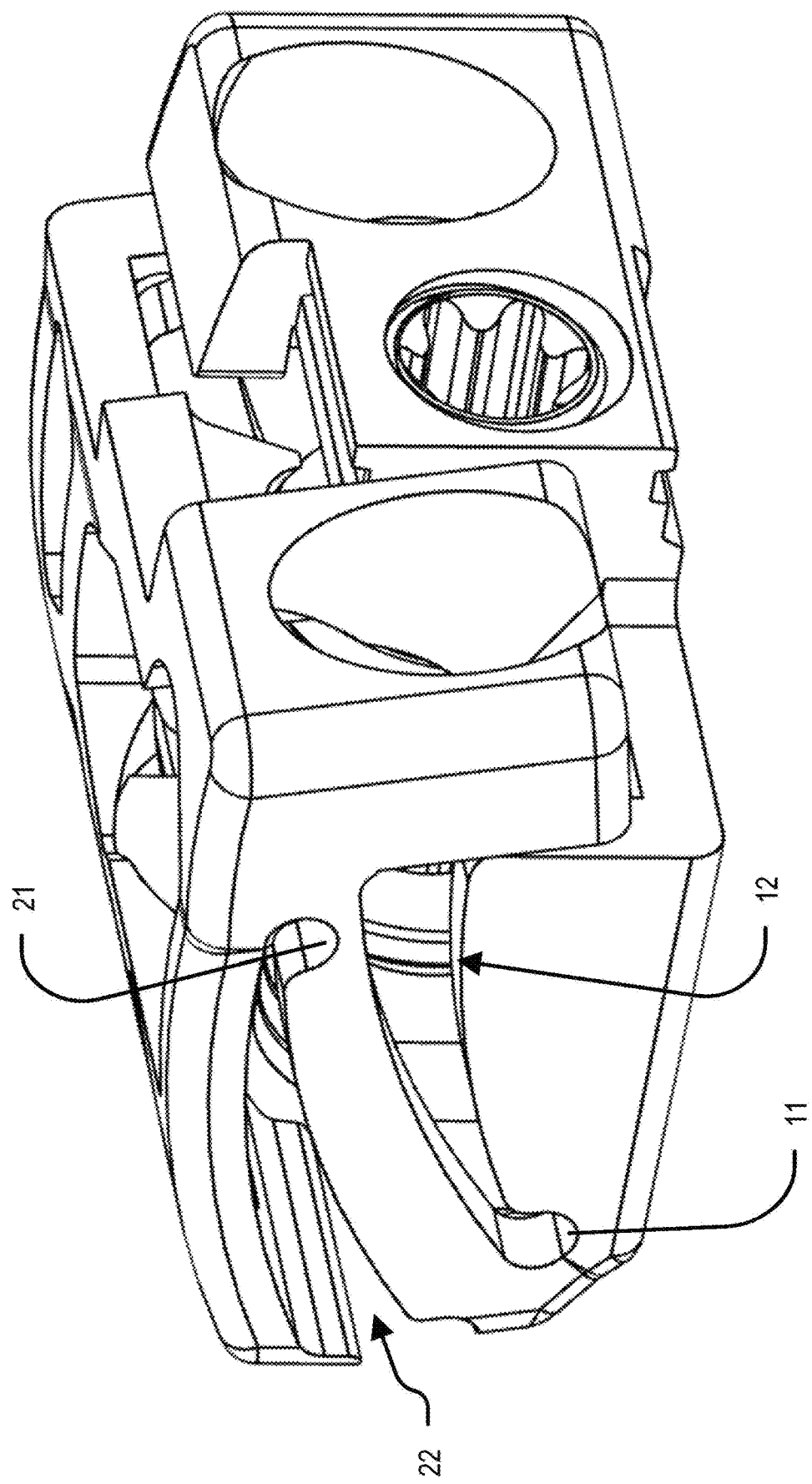
FIG. 15 is a perspective view of a unibody implant in an expanded configuration.
Figure 16:
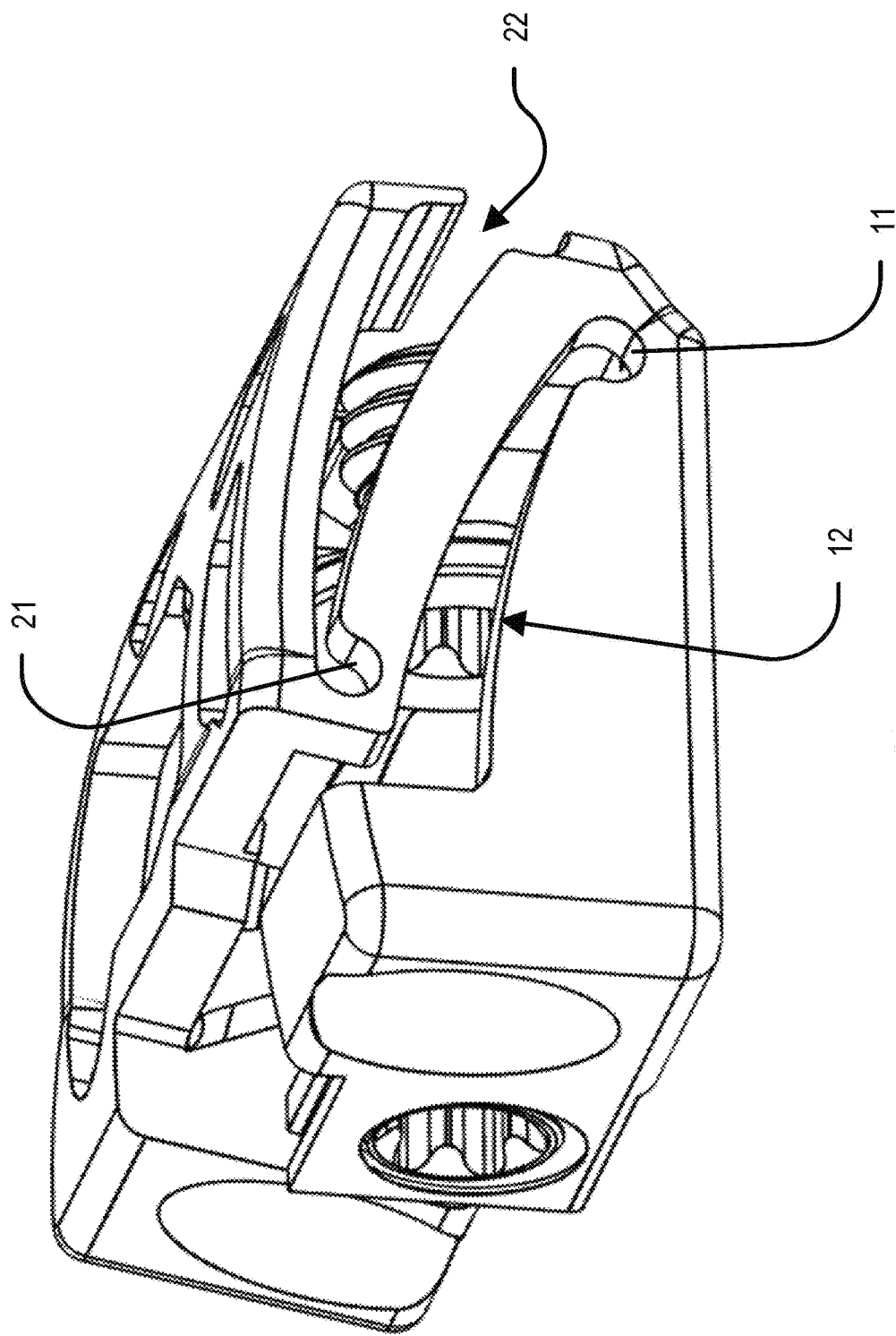
FIG. 16 is an alternate perspective view of a unibody implant in an expanded configuration.

FIGS. 15 and 16 are perspective views of a unibody implant 100 in an expanded configuration. Consistent with the disclosure herein, an end user may have expanded the implant 100 at the proximal side 100p and distal side 100d by rotating the first set screw 40 and second set screw 50, for example. In the example illustration, it is shown that the first seam 12 defines an enlarged discontinuity between the inferior portion 10 and medial portion 20, for example. Similarly, it is shown that the second seam 22 defines an enlarged discontinuity between the medial portion 20 and superior portion 30.

Figure 17:
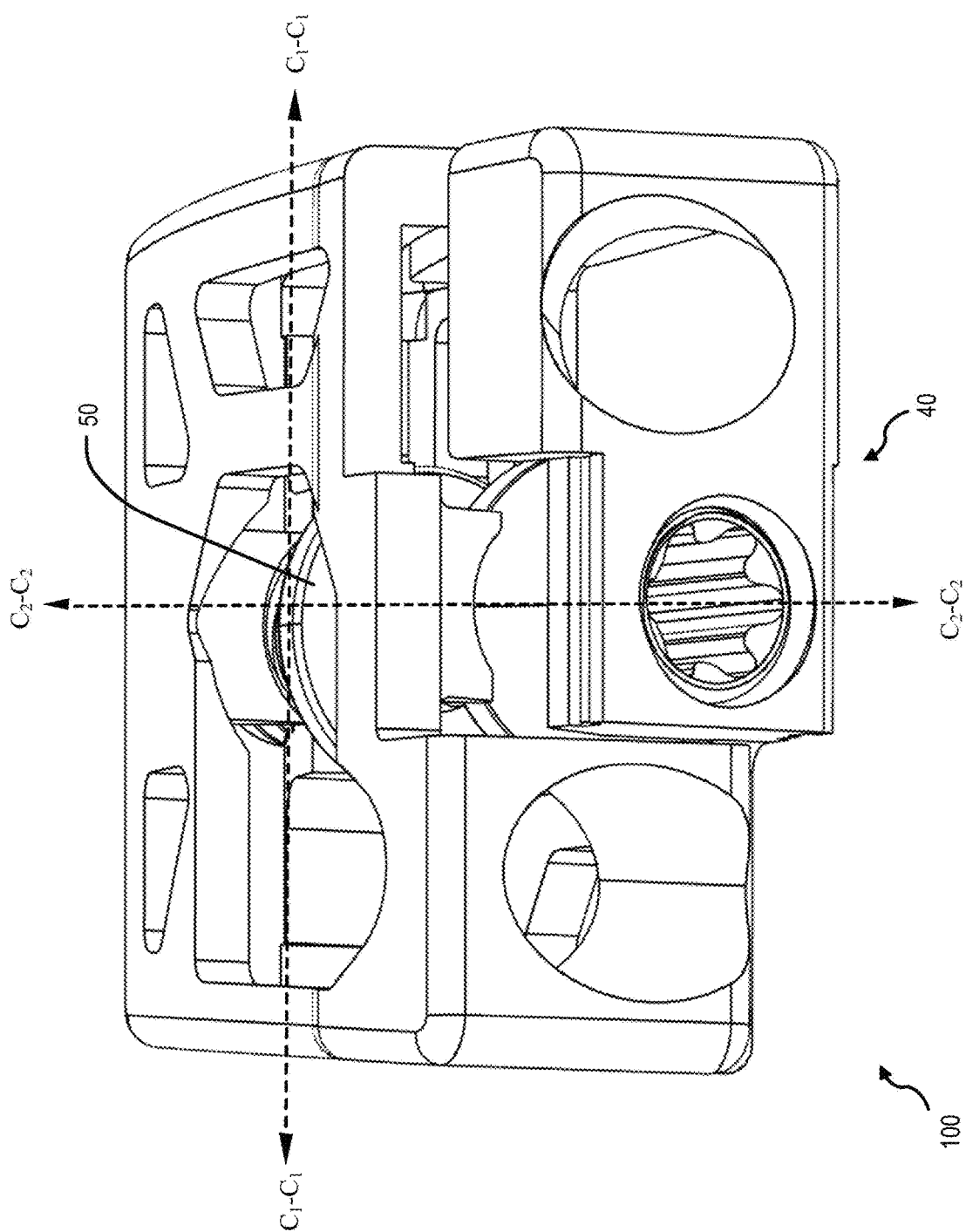
FIG. 17 is a top down front view of a unibody implant in an expanded configuration.
Figure 18:
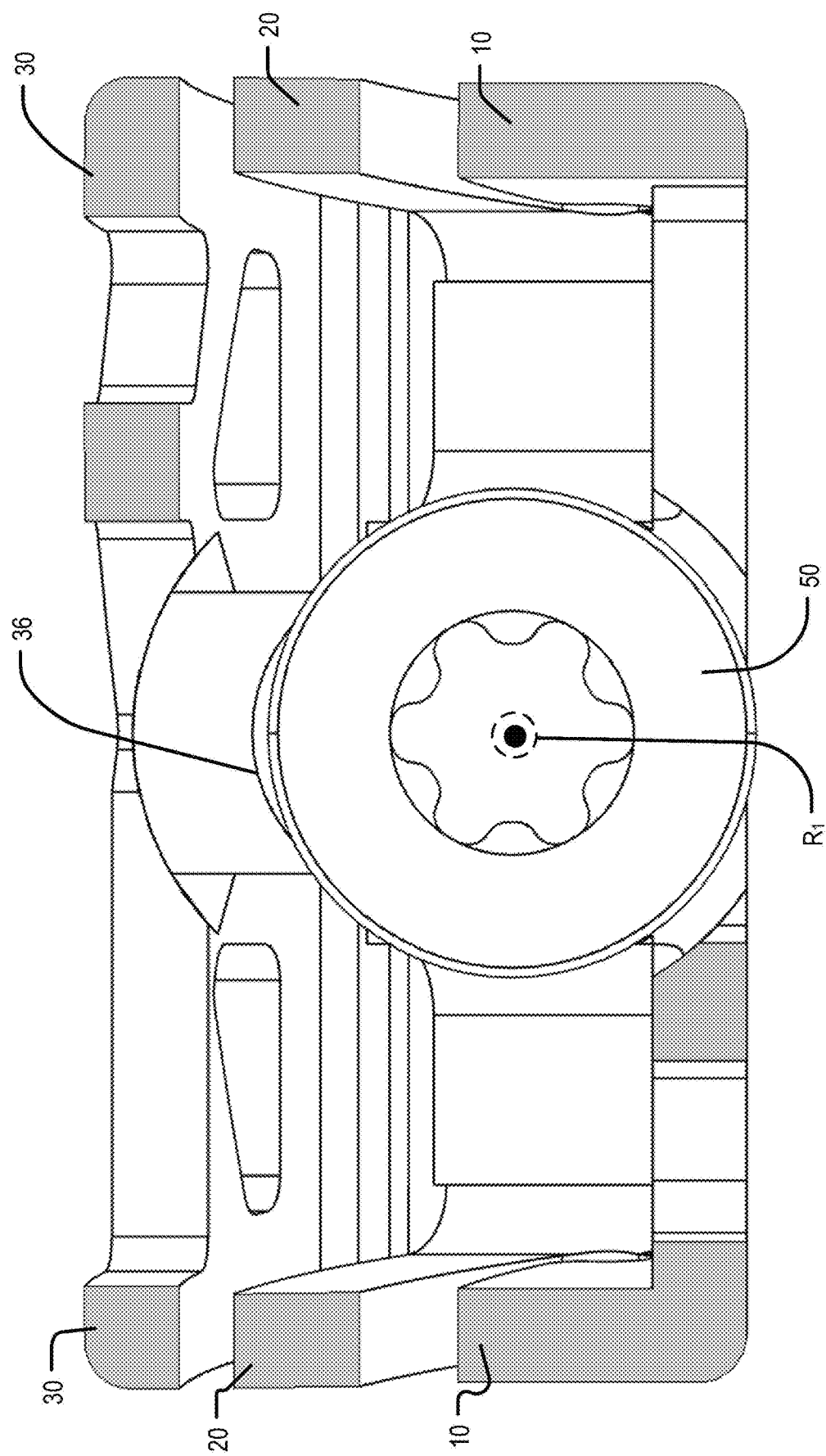
FIG. 18 is a cross section view taken along line $C_1$-$C_1$ of FIG. 17.
Figure 19:
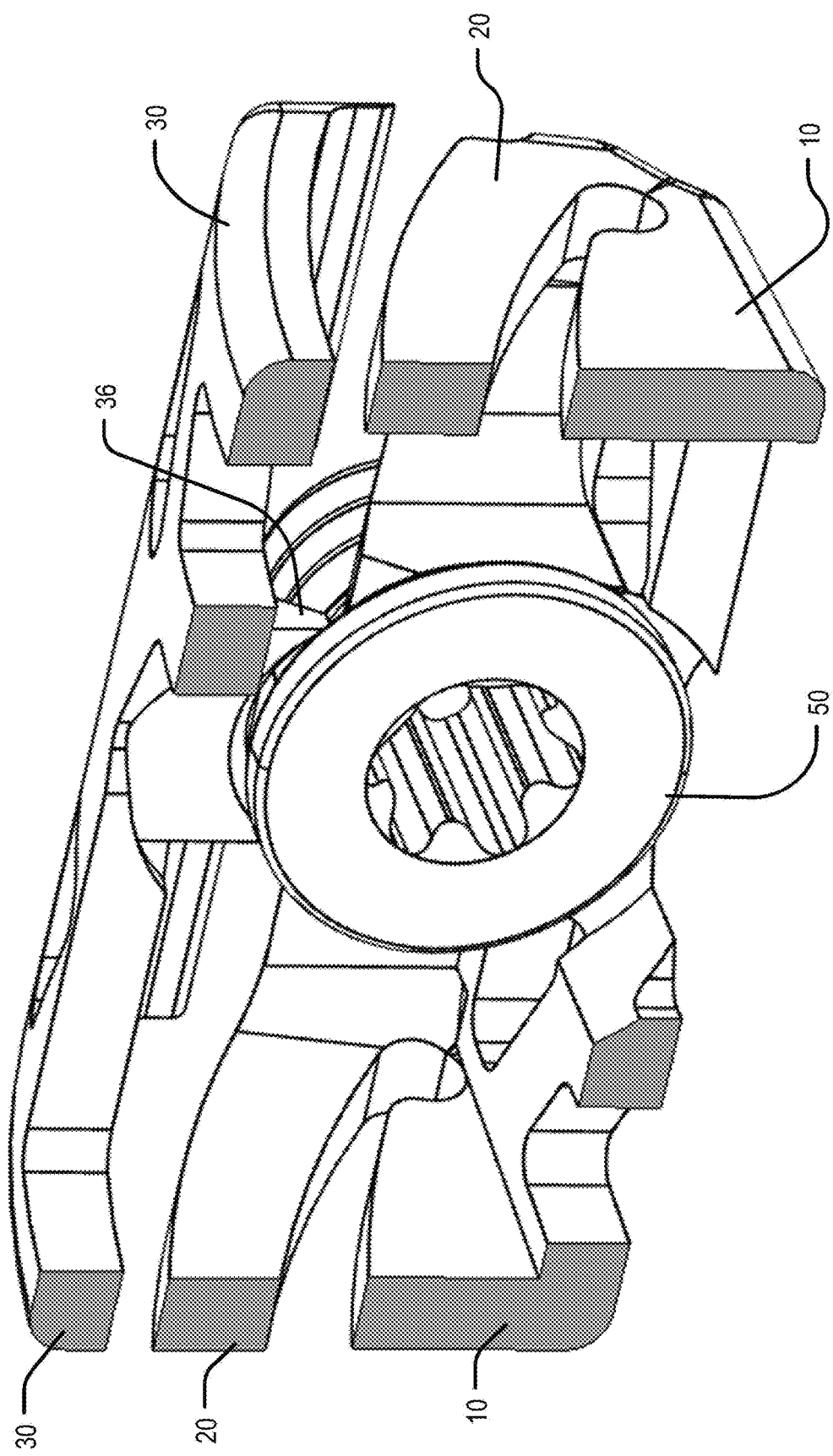
FIG. 19 is a perspective sectional view taken along line $C_1$ of FIG. 17.

FIG. 17 is a top down front view of a unibody implant in an expanded configuration showing a first cross section line in the lateral direction through the second set screw 50 along line $C_1$-$C_1$ and a second cross section line $C_2$-$C_2$ in the longitudinal direction through both the first set screw 40 and second set screw 50. FIG. 18 is a cross section view taken along line $C_1$-$C_1$ and FIG. 19 is a perspective sectional view taken along line $C_1$-$C_1$ of FIG. 17. In the example embodiment, it is shown that by rotating the second set screw 50 about the rotation axis $R_1$ the second set screw 50 has moved towards the distal end 100d within the threaded aperture 17 of the inferior portion 10. In doing so, the inclined surface 56 of second set screw 50 has acted against the inclined ramp 36 of the superior portion 30 and has pushed the superior portion 30 upwards and away from the inferior portion 10. Furthermore, the seams 22 and teardrop shaped cutout 21 on each lateral side surface 100l the superior portion have facilitated the upward and away pivoting of the superior portion 30 with respect to the inferior portion 10 at the distal side 100d. For example, the discontinuity defined by the seams 22 and teardrop shaped cutout 21 are greater in the expanded configuration than in the contracted configuration.

Figure 20:
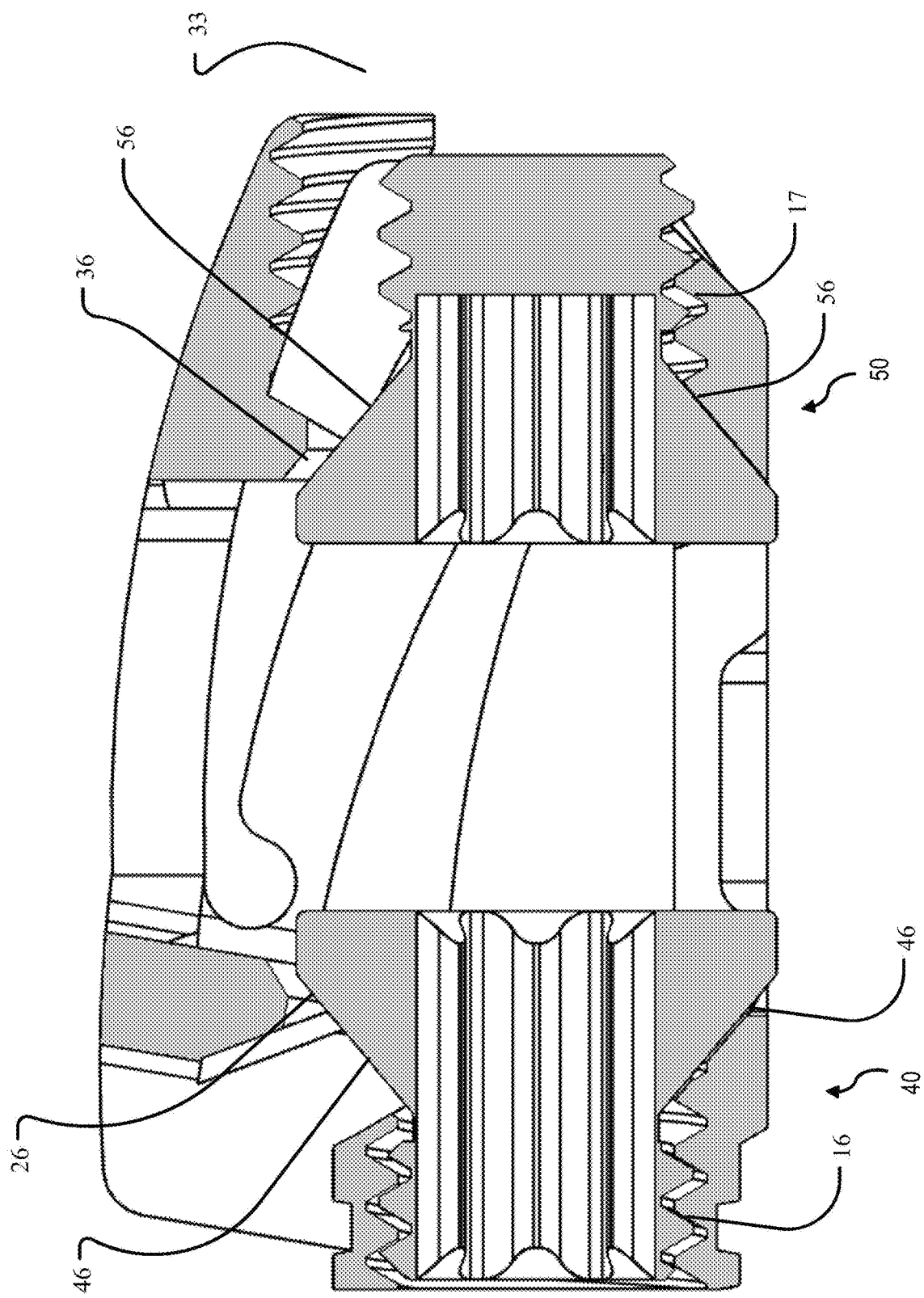
FIG. 20 is a cross section view taken along line $C_2$-$C_2$ of FIG. 17.
Figure 21:
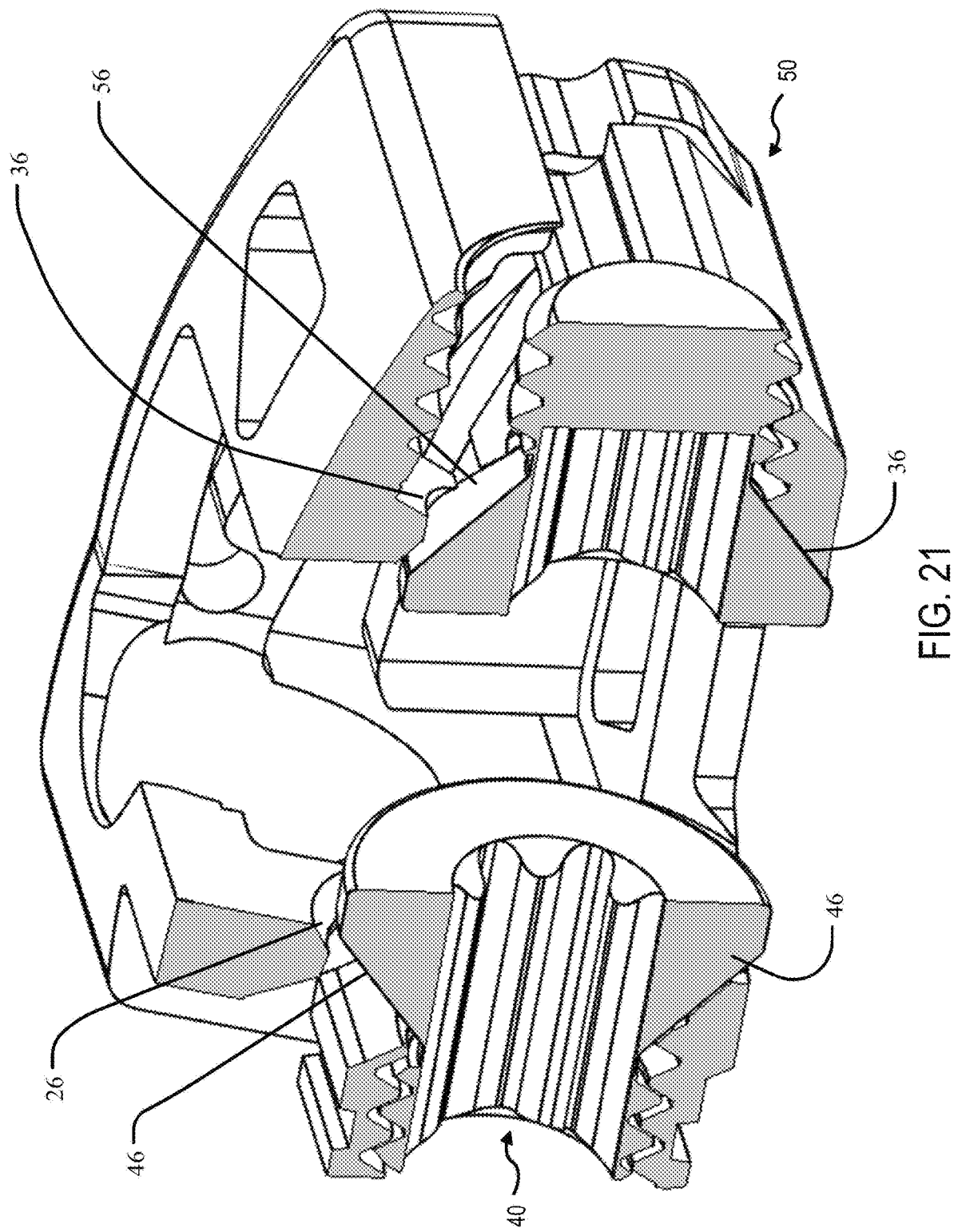
FIG. 21 is a perspective sectional view taken along line $C_2$-$C_2$ of FIG. 17.

FIG. 20 is a cross section view taken along line $C_2$-$C_2$ and FIG. 21 is a perspective sectional view taken along line $C_2$-$C_2$ of FIG. 17. In the example illustration, it is shown that the implant 100 is in an expanded position and each of the set screws 40, 50 have moved away from a medial position of the center of the implant 100 towards the proximal side 100p and distal side 100d, respectively. Consistent with the disclosure herein, the first set screw 40 has been rotated such that it has moved forward towards the proximal side 100p within first threaded aperture 16. In doing so, the inclined surface 46 of first set screw 40 has acted against the inclined ramp 26 thereby pushing the medial portion 20 upwards and away from the inferior portion 10. Furthermore, due to seams 12 and teardrop shaped cutout 11 on each lateral side surface 100l the medial portion 20 may pivot upward and away from the inferior portion 10 at the proximal side 100p, for example. Similarly, the second set screw 50 has been rotated such that it has moved forward towards the distal side 100d within second threaded aperture 17. In doing so, the inclined surface 56 of second set screw 50 has acted against the inclined ramp 36 thereby pushing the superior portion 30 upwards and away from the inferior portion 10. Additionally, it is shown that the third threaded aperture 33 of the superior portion is no longer engaged with the second set screw 50 due to the superior portion 30 being pushed upwards and away from the inferior portion 10. In various embodiments, the first and second set screws 40, 50 are secured to the inferior portion 10 at the first threaded aperture 16 and second threaded aperture 17. Therefore, an expansion of the implant 100 is relative to the inferior portion 10 because the medial portion 20 and superior portion 30 move away and towards the inferior portion 10 as explained above.

Figure 22:
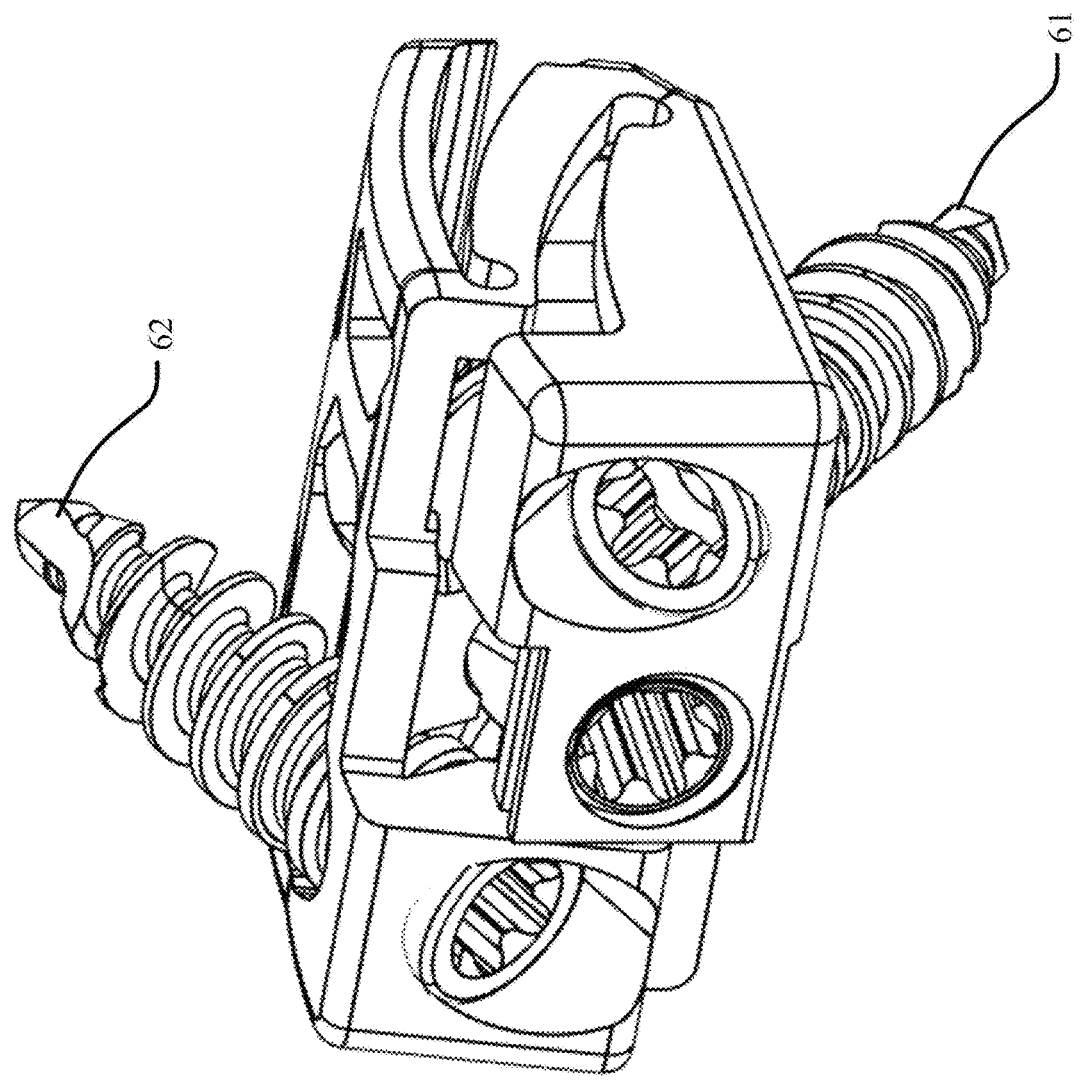
FIG. 22 is a perspective view of a unibody implant in an expanded configuration with a pair of bone screws.
Figure 23:
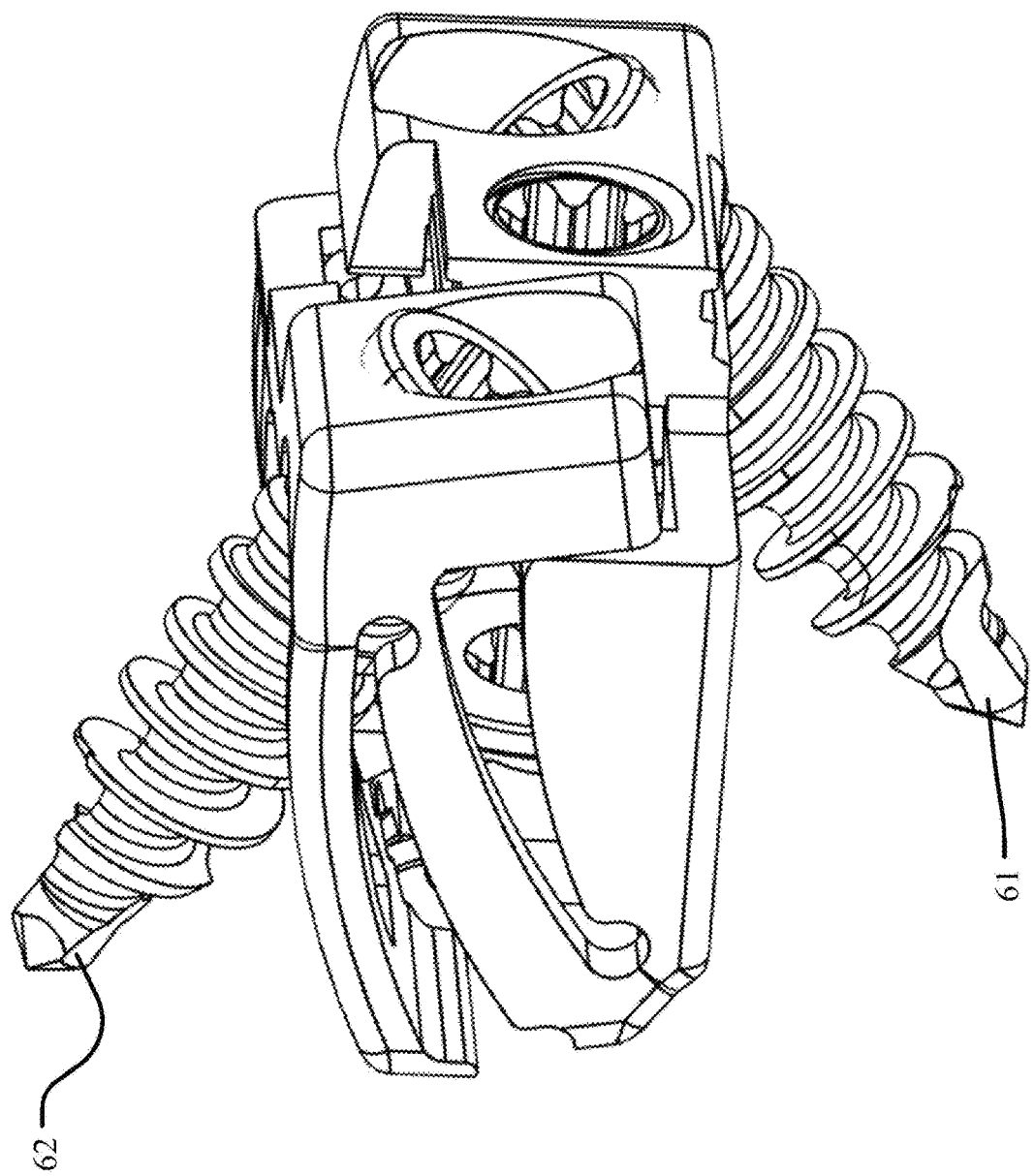
FIG. 23 is an alternate perspective view of a unibody implant in an expanded configuration with a pair of bone screws.

FIG. 22 is a perspective view of a unibody implant in an expanded configuration with a pair of bone screws and FIG. 23 is an alternate perspective view of a unibody implant in an expanded configuration with a pair of bone screws. In the example illustration, it is shown that a first bone screw 61 extends through the first bone screw aperture 14 of the inferior portion 10. For example, the first bone screw 61 extends through the vertical surface of the inferior portion at the proximal side 100p and through the bottom surface of the inferior portion 10. The first bone screw aperture 14 orients the first bone screw 61 along a trajectory projecting towards the distal end 100d that is inclined with respect to the bottom surface of the inferior portion 10. Similarly, a second bone screw 62 extends through the second bone screw aperture 24 of the medial portion 20. For example, the second bone screw 62 extends through the vertical surface of the medial portion 20 at the proximal side 100p and through the top surface of the implant 100. The second bone screw aperture 24 orients the second bone screw 62 along a trajectory projecting towards the distal end 100d that is inclined with respect to the top surface of the implant 100.

In various embodiments, it is contemplated that the implant 100 may be filled with a bone growth promoting material that is either solid or fluid and flowable. In at least one embodiment, a flowable bone growth promoting material may be injected through the hollow first set screw 40 and into the interior of implant 100. Additionally, in various embodiments bone graft may be injected through the hollow central axis of the inner sleeve 211, through the interior of the first screw 40 and into a central internal cavity of the implant 100. In various embodiments, bone graft may be injected after the implant 100 has been expanded into a target configuration and secured between adjacent vertebrae, for example. Furthermore, in various embodiments care may be taken to include flexible covers on the outside lateral side surfaces 100l of implant 100 or on the inside lateral surfaces 100l to contain the flowable bone growth promoting material from leaking out of the discontinuity between the seams and teardrop shaped cutouts 11, 12, 21, and 22, for example. In various embodiments, a surgeon may also pre-pack the interior of the implant 100 with a bone graft or the like, and inject flowable bone growth promoting material after placement of the implant 100 to fill in the remaining voids.

Figure 24:
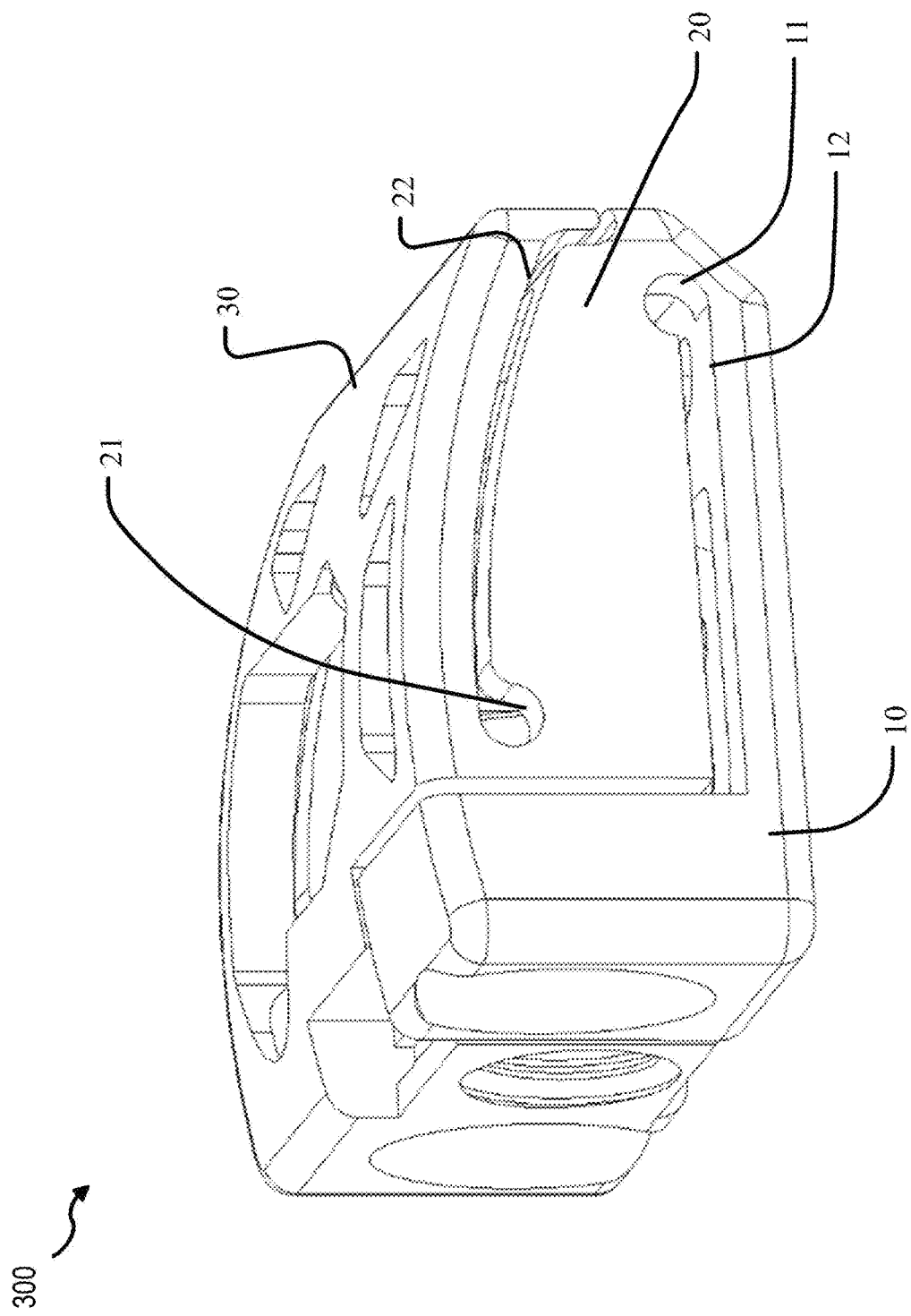
FIG. 24 is a perspective view of a unibody implant in a contracted configuration.
Figure 25:
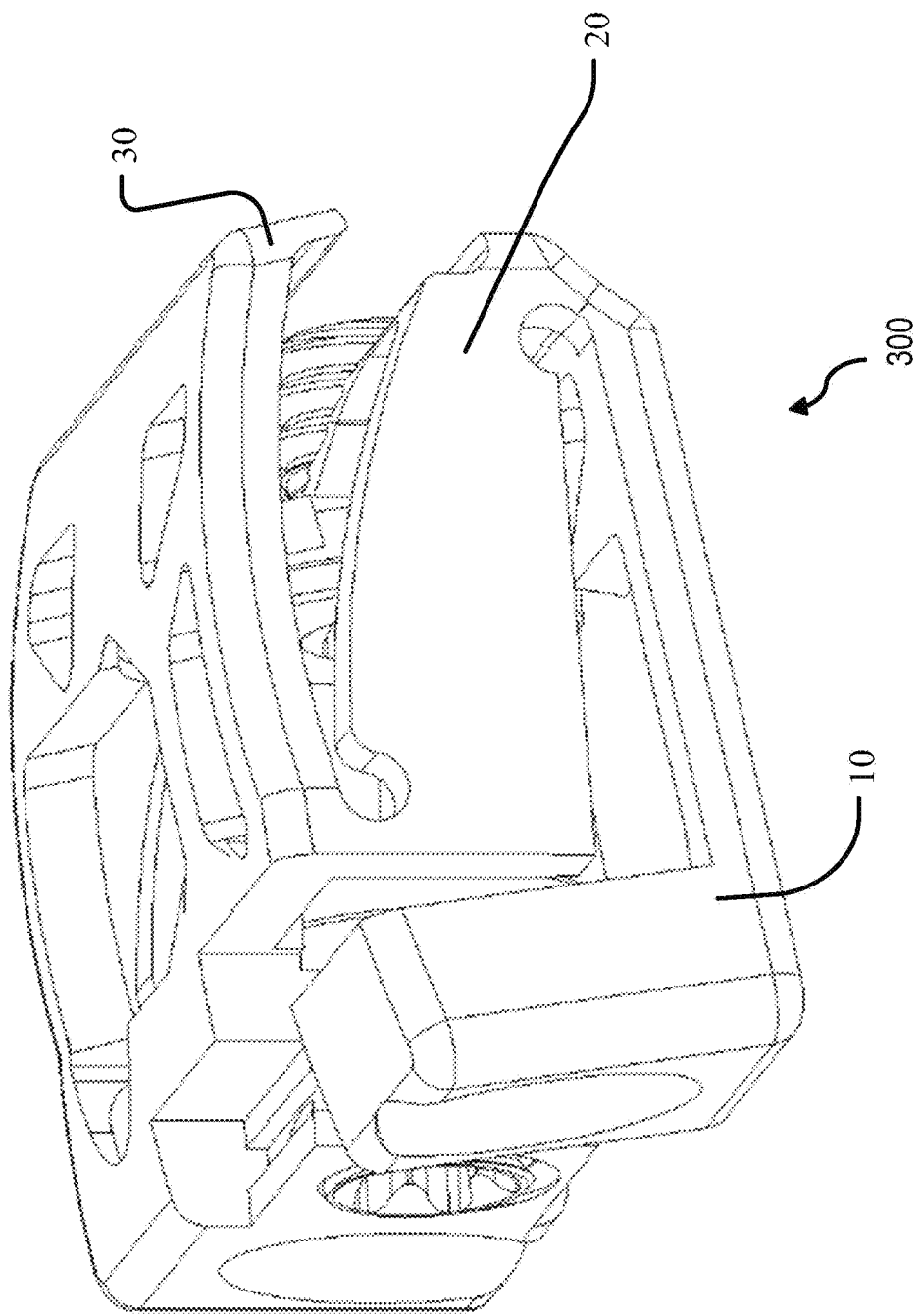
FIG. 25 is a perspective view of a unibody implant in an expanded configuration.

Referring generally to FIGS. 24-27 an alternate embodiment of a unibody implant 300 is disclosed. FIG. 24 is a perspective view of a unibody implant 300 in a contracted configuration and FIG. 25 is a perspective view of a unibody implant 300 in an expanded configuration. Unibody implant 300 may include the same, substantially the same, and/or similar features as explained above previously with respect to unibody implant 100, for example. Unibody implant 300 may differ from unibody implant 100 in that the first set screw 40 and second set screw 50 may be supported by the medial portion 20 and act against a superior ramp 301 and an inferior ramp 303, for example. In various embodiments, the first set screw 40 and second set screw 50 may remain coupled to medial portion 20 and supported with respect to medial portion 20 while urging the inferior portion 10 and superior portion 30 away from medial portion 20, for example. Unibody implant 300 may have a relatively larger medial portion 20 and smaller inferior portion 10, at least relative to implant 100, for example. Unibody implant 300 may include seams 12, 22 and tear drop cutouts 11, 21 that are similar to those previously described with respect to unibody implant 100.

Figure 26:
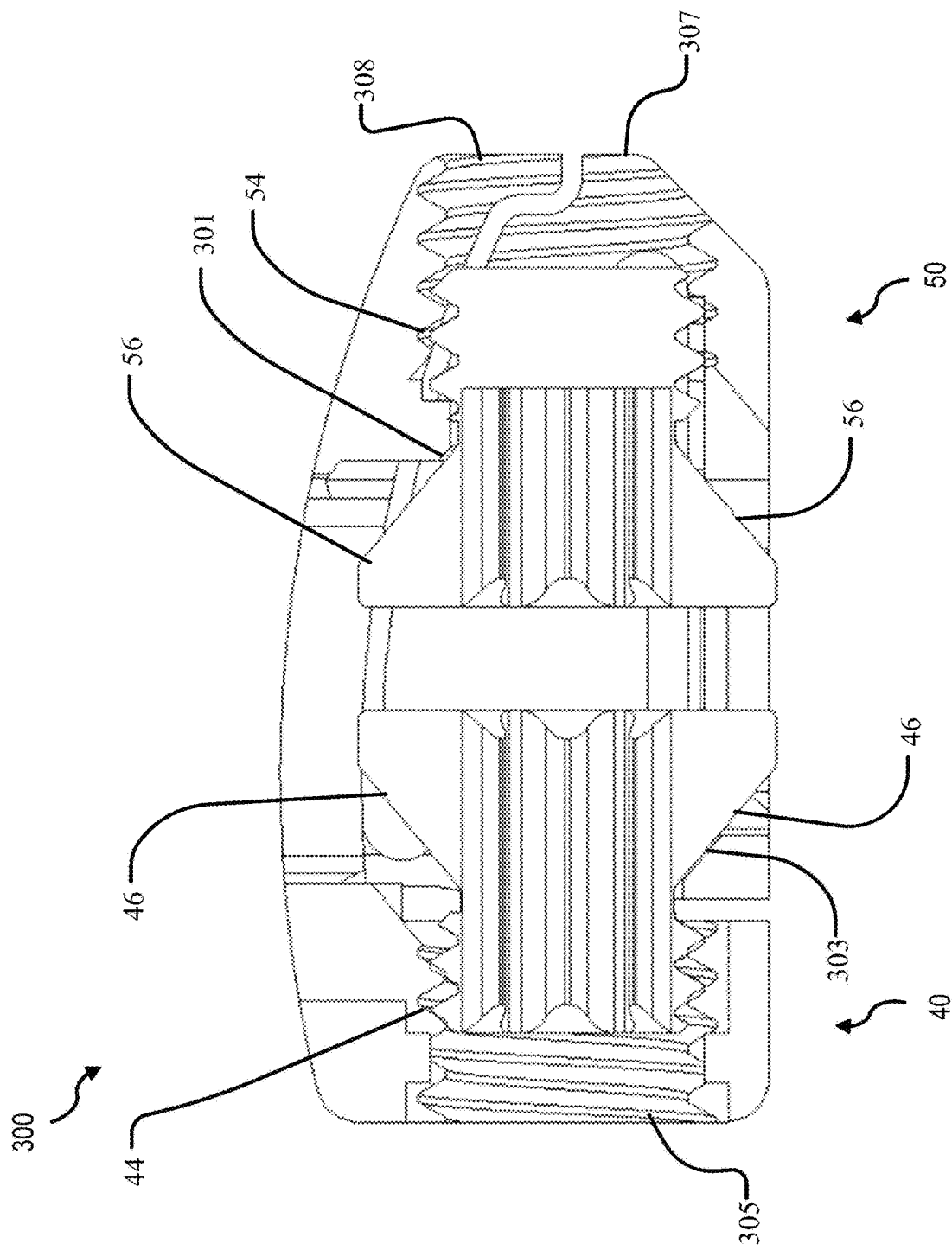
FIG. 26 is a cross section view of the implant of FIG. 24.
Figure 27:
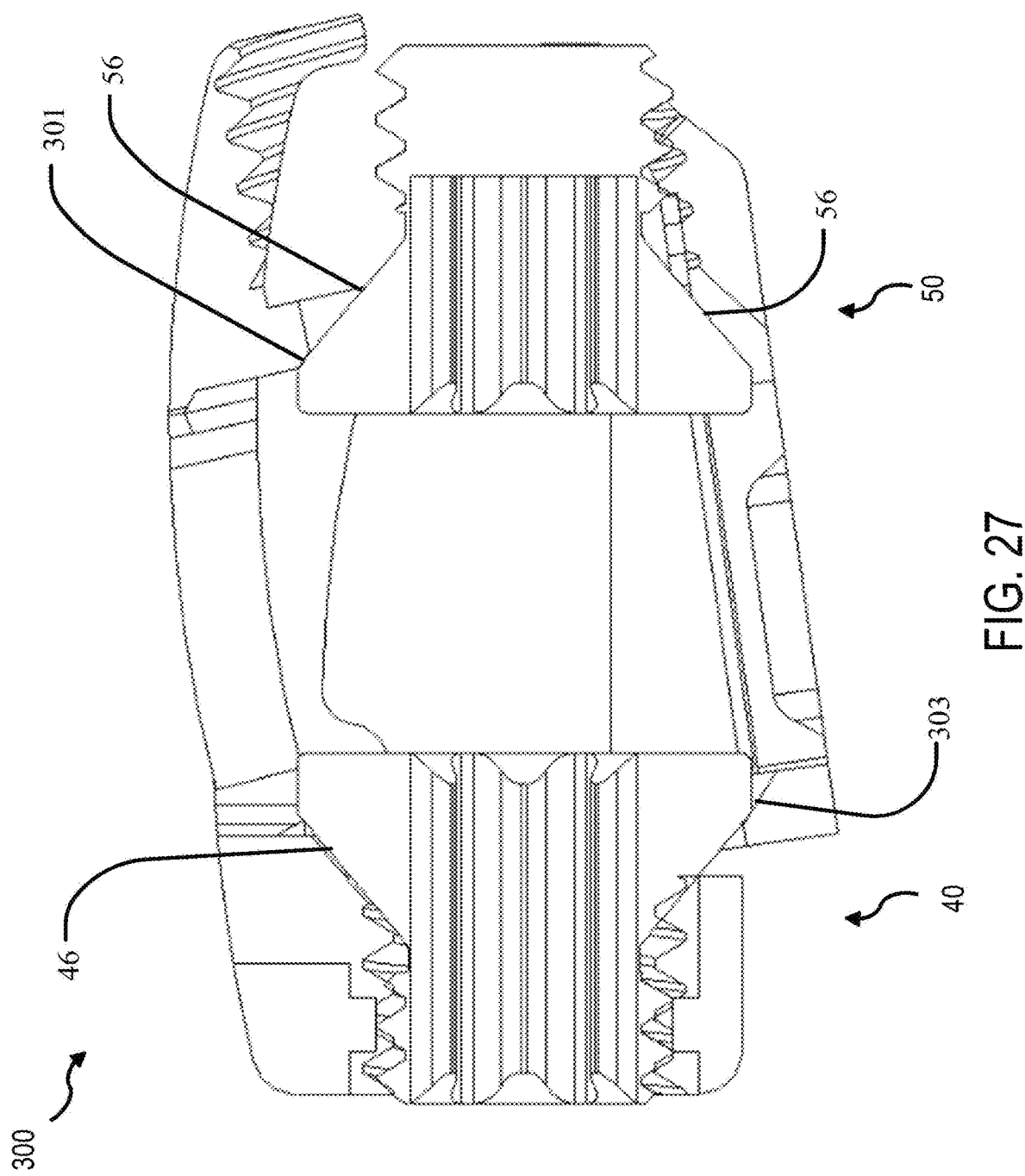
FIG. 27 is a cross section view of the implant of FIG. 25.

FIG. 26 is a cross section view of unibody implant 300 in a contracted configuration and FIG. 27 is a cross section view of unibody implant 300 in an expanded configuration. Each cross section view may extend from a proximal end through the center of implant 300 to a distal end, for example. In the example embodiment, first set screw 40 may act against an inferior ramp 303 of the inferior portion 10 and second set screw 50 may act against a superior ramp 301 of the superior portion 30, for example. In this way, when rotating the first set screw 40 from a medial position (shown in FIG. 26) towards the proximal end of implant 300, the first set screw 40 pushes against the inclined inferior ramp 301 while remaining axially retained within first medial threaded aperture 305 thereby pushing the inferior portion 10 away from the medial portion 20 (shown in FIG. 27) Similarly, when rotating the second set screw 50 from a medial position (shown in FIG. 26) towards the distal end of implant 300, the second set screw 50 pushes against the inclined superior ramp 303 while remaining axially retained within second medial threaded aperture 307. Additionally, in various embodiments, in the collapsed configuration second set screw 50 may also be engaged with superior threaded portion 308 in similar manner as the second threaded aperture 17 and third threaded 33 of unibody implant 100, for example. Furthermore, in various embodiments, in the expanded configuration second set screw 50 may only be engaged with medial threaded aperture 307 as shown in FIG. 27 due to superior portion 30 being pushed away from medial portion 20, for example.

At least one advantage of having the first and second set screws 40, 50 remain axially aligned with respect to medial portion 20 may be greater range in expansion and inclination due to the operability of being able to independently adjust an inclination of inferior portion 10 and/or superior portion 30 with respect to medial portion 20. For example, an end user can independently adjust the expansion and inclination of inferior portion 10 with respect to medial portion 20 and independently adjust the expansion and inclination of superior 30 with respect to medial portion 20. For example, the inferior portion 10 may be pushed away from medial portion 20 while medial portion 20 supports inferior portion via set screw 40 and inclined inferior ramp 303. Similarly, the superior portion 30 may be pushed away from medial portion 20 while medial portion 20 supports superior portion 30 via set screw 50 and inclined superior ramp 301. The inclined superior ramp 301 and inclined inferior ramp 303 may have the same, substantially the same, and/or similar geometry and size as the first inclined ramp 26 and second inclined ramp 36 as explained above with respect to unibody implant 100.

Figure 28:
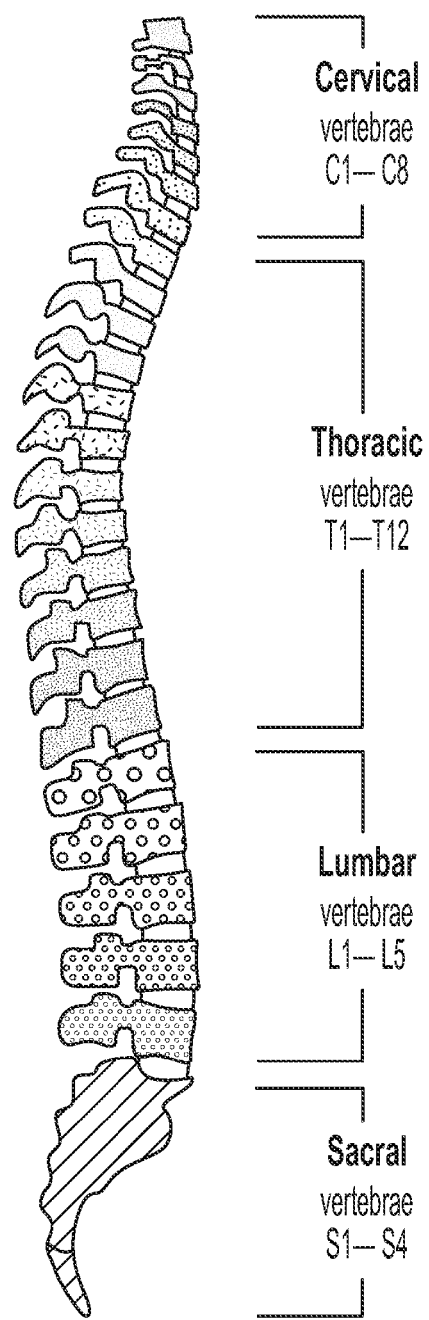
Figure 29:
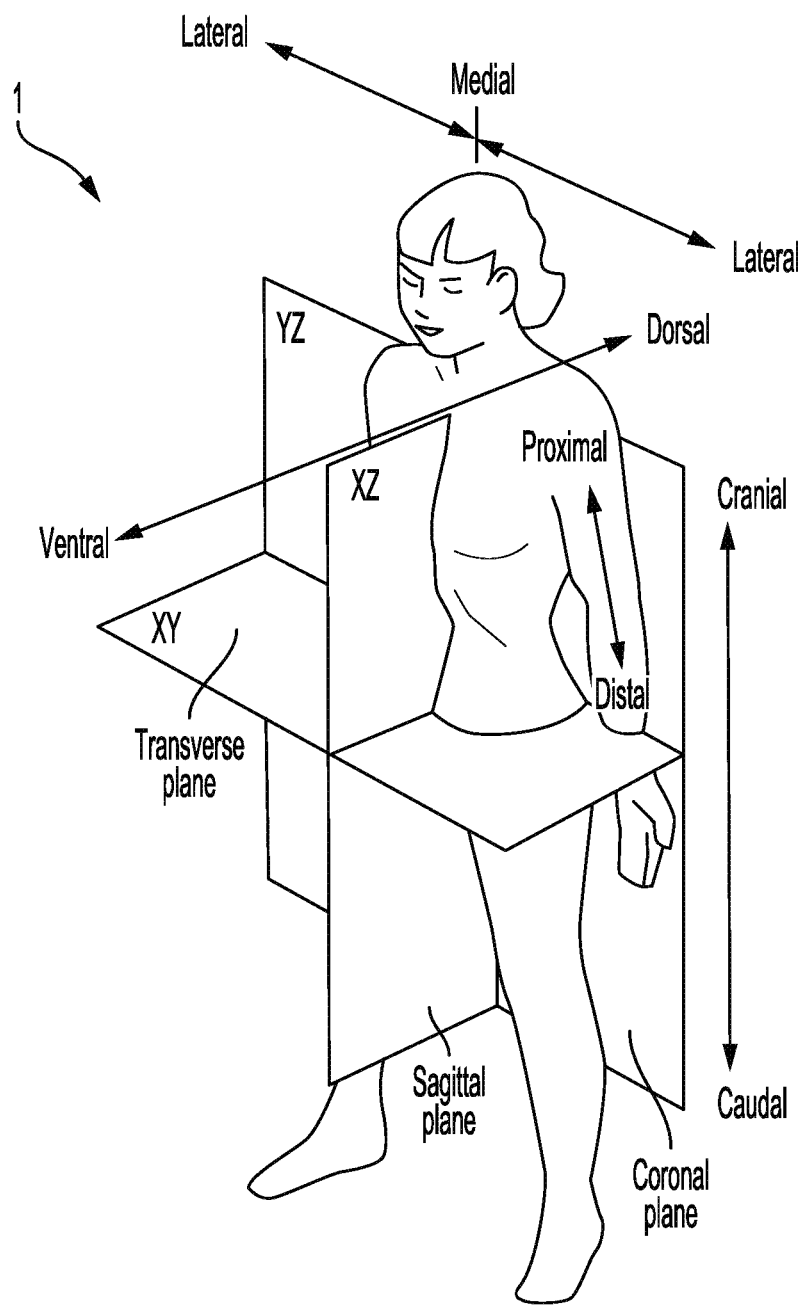

FIG. 28 is a reference drawing showing the human spine of which various disclosed implant embodiments may be installed in. FIG. 29 is a reference drawing showing various planes and reference directions of which the various disclosed implant embodiments may move in or act in with respect to a patient 1.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

What is claimed is:

1. A unibody implant movable between an expanded position and a contracted position, comprising:
    a unitary expandable body extending from a proximal side to a distal side in a longitudinal direction, extending from a first lateral side to a second lateral side in a lateral direction, and extending from a superior side to an inferior side in a vertical direction,
    the unitary expandable body being defined by an inferior portion, a superior portion, and a medial portion, the inferior portion being connected to the medial portion and the medial portion being connected to the superior portion;
    a first set screw and a second set screw rotatably supported by the body and rotatable in a clockwise direction and counterclockwise direction around a rotation axis that extends parallel to the longitudinal direction, the first set screw having a first inclined surface facing the proximal side and the second set screw having a second inclined surface facing the distal side;
    wherein:
        the medial portion comprises a first inclined ramp disposed on an interior surface thereof and facing the first inclined surface of the first set screw,
        the superior portion comprises a second inclined ramp disposed on an interior surface thereof and facing the second inclined surface of the second set screw,
        the first set screw is movable in the longitudinal direction towards the proximal side or away from the proximal side upon rotation of the first set screw along the rotation axis and the second set screw is movable in the longitudinal direction towards the distal side and away from the distal side upon rotation of the second set screw along the rotation axis,
        in an unexpanded position, the first set screw and second set screw are disposed in a medial position with respect to the proximal side and distal side,
        in a first expanded position, the first set screw is disposed proximate the proximal side relative to the unexpanded position and the first inclined surface of the first set screw supports the first inclined ramp such that a vertical distance of the body between the superior and inferior sides of the body adjacent the proximal side of the body is greater than in the unexpanded position, and
        in a second expanded position, the second set screw is disposed proximate the distal side relative to the unexpanded position and the second inclined surface of the second set screw supports the second inclined ramp such that a vertical distance of the body between the superior and inferior sides of the body adjacent the distal side of the body is greater than in the unexpanded position.

2. The unibody implant of claim 1, wherein the inferior portion comprises a first threaded aperture rotatably supporting the first set screw and a second threaded aperture rotatably supporting the second set screw.

3. The unibody implant of claim 1, wherein:
    the inferior portion comprises a first threaded aperture rotatably supporting the first set screw and a second threaded aperture rotatably supporting a first portion of the second set screw, and
    the superior portion comprises a third threaded aperture rotatably supporting a second portion of the second set screw.

4. The unibody implant of claim 1, wherein the first inclined surface is conically shaped and the second inclined surface is conically shaped.

5. The unibody implant of claim 4, wherein:
    the first inclined ramp comprises a first curved surface extending towards the first lateral side and second lateral side that tapers towards the proximal side, the first curved surface being frictionally engaged with the first inclined surface of the first set screw, and
    the second inclined ramp comprises a second curved surface extending towards the first lateral side and second lateral side that tapers towards the distal side, the second curved surface being frictionally engaged with the second inclined surface of the second set screw.

6. The unibody implant of claim 1, wherein the inferior portion is connected to the medial portion by the first lateral side and second lateral side proximate the distal side such that a first lateral seam is formed as a first discontinuity on the first lateral side between the inferior portion and the medial portion and a second lateral seam is formed as a second discontinuity on the second lateral side between the inferior portion and the medial portion.

7. The unibody implant of claim 6, wherein the first discontinuity comprises a first teardrop cutout proximate the distal side and the second discontinuity comprises a second teardrop cutout proximate the distal side.

8. The unibody implant of claim 6, wherein the medial portion is connected to the superior portion by the first lateral side and second lateral side proximate the proximal side such that a third lateral seam is formed as a third discontinuity on the first lateral side between the medial portion and superior portion and a fourth lateral seam is formed as a fourth discontinuity on the second lateral side between the medial portion and superior portion.

9. The unibody implant of claim 8, wherein the third discontinuity comprises a third teardrop cutout proximate the proximal side and the second discontinuity comprises a fourth teardrop cutout proximate the proximal side.

10. The unibody implant of claim 1, wherein:
    the inferior portion is connected to the medial portion by the first lateral side and second lateral side proximate the distal side such that a first lateral seam is formed as a first discontinuity on the first lateral side between the inferior portion and the medial portion and a second lateral seam is formed as a second discontinuity on the second lateral side between the inferior portion and the medial portion, and
    the medial portion is connected to the superior portion by the first lateral side and second lateral side proximate the proximal side such that a third lateral seam is formed as a third discontinuity on the first lateral side between the medial portion and superior portion and a fourth lateral seam is formed as a fourth discontinuity on the second lateral side between the medial portion and superior portion.

11. The unibody implant of claim 10, wherein:
the first discontinuity comprises a first teardrop cutout proximate the distal side and the second discontinuity comprises a second teardrop cutout proximate the distal side, and
the third discontinuity comprises a third teardrop cutout proximate the proximal side and the second discontinuity comprises a fourth teardrop cutout proximate the proximal side.

12. The unibody implant of claim 1, wherein the proximal side is defined by a first vertical surface of the inferior portion and a second vertical surface of the medial portion.

13. The unibody implant of claim 12, wherein the first vertical surface comprises an access aperture providing access to the first set screw and the second set screw.

14. The unibody implant of claim 13, wherein the inferior portion comprises a first bone screw aperture extending from the first vertical surface of the inferior portion and through a bottom surface of the inferior portion, the first bone screw aperture defining a first bone screw trajectory projecting towards the distal side that is inclined with respect to the bottom surface of the inferior portion.

15. The unibody implant of claim 14, wherein the second vertical surface comprises a second bone screw aperture extending from the second vertical surface of the medial portion and through a top surface of the superior portion, the second bone screw aperture defining a second bone screw trajectory projecting towards the distal side that is inclined with respect to the top surface of the superior portion.

16. The unibody implant of claim 1, wherein the first set screw comprises a first hollow interior including a first circumferential interior surface having a first plurality of projections and valleys and the second set screw comprises a second hollow interior including a second circumferential interior surface having a second plurality of projections and valleys.

17. The unibody implant of claim 1, wherein the first set screw and second set screw are coaxially aligned.

18. The unibody implant of claim 1, wherein the first set screw and second set screw comprise a coaxially aligned hollow interior including a plurality of projections and valleys, respectively.

19. A system for expanding and contracting a unibody implant, comprising:
a unibody implant movable between an expanded position and a contracted position, comprising:
a unitary expandable body extending from a proximal side to a distal side in a longitudinal direction, extending from a first lateral side to a second lateral side in a lateral direction, and extending from a superior side to an inferior side in a vertical direction,
the unitary expandable body being defined by an inferior portion, a superior portion, and a medial portion, the inferior portion being connected to the medial portion and the medial portion being connected to the superior portion;
a first set screw and a second set screw rotatably supported by the body and rotatable in a clockwise direction and counterclockwise direction around a rotation axis that extends parallel to the longitudinal direction, the first set screw having a first inclined surface facing the proximal side and the second set screw having a second inclined surface facing the distal side;
wherein:
the medial portion comprises a first inclined ramp disposed on an interior surface thereof and facing the first inclined surface of the first set screw,
the superior portion comprises a second inclined ramp disposed on an interior surface thereof and facing the second inclined surface of the second set screw,
the first set screw is movable in the longitudinal direction towards the proximal side or away from the proximal side upon rotation of the first set screw along the rotation axis and the second set screw is movable in the longitudinal direction towards the distal side and away from the distal side upon rotation of the second set screw along the rotation axis,
movement of the first set screw in the longitudinal direction towards the proximal side urges the first inclined surface against the first inclined ramp thereby expanding a vertical distance of the body between the superior and inferior sides of the body adjacent the proximal side of the body,
movement of the second set screw in the longitudinal direction towards the distal side urges the second inclined surface against the second inclined ramp thereby expanding a vertical distance of the body between the superior and inferior sides of the body adjacent the distal side of the body,
the first set screw comprises a first hollow interior including a first circumferential interior surface having a first plurality of projections and valleys and the second set screw comprises a second hollow interior including a second circumferential interior surface having a second plurality of projections and valleys,
an inserter having a rotatable drive end extending at least a first distance in a longitudinal direction corresponding to a length of the first circumferential interior surface, the rotatable drive end having a third plurality of projections and valleys corresponding in size and shape to the first plurality of projections and valleys,
wherein the inserter is configured to rotate:
either one of the first set screw and second set screw at a time, and/or
both of the first set screw and second set screw at the same time.

20. A method for expanding and contracting a unibody implant, comprising:
providing a unibody implant movable between an expanded position and a contracted position, comprising:
a unitary expandable body extending from a proximal side to a distal side in a longitudinal direction, extending from a first lateral side to a second lateral side in a lateral direction, and extending from a superior side to an inferior side in a vertical direction,
the unitary expandable body being defined by an inferior portion, a superior portion, and a medial portion, the inferior portion being connected to the medial portion and the medial portion being connected to the superior portion;
a first set screw and a second set screw rotatably supported by the body and rotatable in a clockwise direction and counterclockwise direction around a rotation axis that extends parallel to the longitudinal direction, the first set screw having a first inclined surface facing the proximal side and the second set screw having a second inclined surface facing the distal side;
wherein:
the medial portion comprises a first inclined ramp disposed on an interior surface thereof and facing the first inclined surface of the first set screw, the superior portion comprises a second inclined ramp disposed on an interior surface thereof and facing the second inclined surface of the second set screw, the first set screw is movable in the longitudinal direction towards the proximal side or away from the proximal side upon rotation of the first set screw along the rotation axis and the second set screw is movable in the longitudinal direction towards the distal side and away from the distal side upon rotation of the second set screw along the rotation axis, movement of the first set screw in the longitudinal direction towards the proximal side urges the first inclined surface against the first inclined ramp thereby expanding a vertical distance of the body between the superior and inferior sides of the body adjacent the proximal side of the body, movement of the second set screw in the longitudinal direction towards the distal side urges the second inclined surface against the second inclined ramp thereby expanding a vertical distance of the body between the superior and inferior sides of the body adjacent the distal side of the body, the first set screw comprises a first hollow interior including a first circumferential interior surface having a first plurality of projections and valleys and the second set screw comprises a second hollow interior including a second circumferential interior surface having a second plurality of projections and valleys, providing an inserter having a rotatable drive end extending at least a first distance in a longitudinal direction corresponding to a length of the first circumferential interior surface, the rotatable drive end having a third plurality of projections and valleys corresponding in size and shape to the first plurality of projections and valleys, wherein the inserter is configured to rotate:
  either one of the first set screw and second set screw at a time, and/or
  both of the first set screw and second set screw at the same time;

positioning the unibody implant in a cervical region of a patient between a superior vertebrae and an inferior vertebrae; and causing at least one of: a lordosis expansion by rotating the first set screw via the drive end of the inserter and a kyphosis expansion by rotating the second set screw via the drive end of the inserter.

* * * * *